US007745585B2

(12) United States Patent
Zophel et al.

(10) Patent No.: US 7,745,585 B2
(45) Date of Patent: Jun. 29, 2010

(54) ANTIBODIES TO INTERLEUKIN-LIKE EPITHELIAL-MESENCHYMAL TRANSITION INDUCER (ILEI)

(75) Inventors: Andreas Zophel, Vienna (AT); Horst Johann Ahorn, Weigelsdorf (AT); Birgit Jung, Laupheim (DE); Renate Konopitzky, Bad Voeslau (AT); Karl-Heinz Heider, Stockerau (AT); Norbert Kraut, Baden (AT); Peter Seither, Lustadt (DE); Thomas Waerner, Vienna (AT); Hartmut Beug, Vienna (AT); Martin Jechlinger, Vienna (AT); Ido M. Tamir, Vienna (AT); Andreas Weith, Eberhardzell (DE); Stefan Gruenert, Vienna (AT)

(73) Assignee: Boehringer Ingelheim International GmbH, Ingelheim (DE)

( * ) Notice: Subject to any disclaimer, the term of this patent is extended or adjusted under 35 U.S.C. 154(b) by 387 days.

(21) Appl. No.: 10/570,448

(22) PCT Filed: Sep. 2, 2004

(86) PCT No.: PCT/EP2004/009790

§ 371 (c)(1),
(2), (4) Date: Dec. 11, 2006

(87) PCT Pub. No.: WO2005/035762

PCT Pub. Date: Apr. 21, 2005

(65) Prior Publication Data

US 2007/0089176 A1    Apr. 19, 2007

(30) Foreign Application Priority Data

Sep. 2, 2003    (EP) .................... 03019551

(51) Int. Cl.
C12P 21/08    (2006.01)
C07K 16/00    (2006.01)
A61K 39/395   (2006.01)
A61K 39/00    (2006.01)

(52) U.S. Cl. .............. 530/387.9; 530/387.3; 530/388.1; 530/388.15; 530/388.22; 530/388.23; 530/389.1; 530/389.2; 530/391.3; 424/130.1; 424/138.1; 424/139.1

(58) Field of Classification Search .............. None
See application file for complete search history.

(56) References Cited

U.S. PATENT DOCUMENTS 6,506,607 B1    1/2003   Shyjan
6,566,078 B1 *  5/2003   Raitano et al. ........... 435/7.1
6,902,911 B1 *  6/2005   Conklin et al. .......... 435/69.8

2004/0137575 A1    7/2004   Conklin

FOREIGN PATENT DOCUMENTS

WO    WO 99/25828 A1    5/1999
WO    WO 99/47658       9/1999
WO    WO 99/56778       11/1999
WO    WO 02/063009 A2   8/2002

OTHER PUBLICATIONS

Zhu, Y. et al; "Cloning, Expression, and Initial Characterization of a Novel Cytokine-like Gene Family"; Genomics, vol. 80, No. 2, 2002; pp. 144-150.
Ohno, I. et al; "The cloning of a cDNA for novel genes expressed in human osteoblasts"; 1998; XP002230218; Database Accession No. D87120.
Strausberg, R. L. et al; "Generation and initial analysis of more than 15,000 full-length human and mouse cDNA sequences"; 2001; XP002269510; Database Accession No. BC009086.
Arnon, et al; "Monoclonal Antibodies For Immunotargeting of Drugs In Cancer Therapy", Monoclonal Antibodies and Cancer Therapy, Reisfeld, et al (eds.)(1985), pp. 243-256.
Baldwin, et al; "Analysis, Results, and Future Prospective of the Therapeutic Use of Radiolabeled Antibody in Cancer Therapy", Academic Press (1985), pp. 303-316.
Bartel, et al; "Isolation of New Ribozymes from a Large Pool of Random Sequnces" (1993) Science 261; pp. 1411-1418.
Bauer, M., et al , "TGFbeta1 in liver fibrosis; time to change paradigms?" FEBS Letters (2001) 502, pp. 1-3.
Beddington, R.S., et al , "Axis development and early asymmetry in mammals." (1999), Cell, 96(2); pp. 195-209.
Beidler, et al., "Cloning and High Level Expression of a Chimeric Antibody With Specificity for Human Carcinoembryonic Antigen"; J Immunol (1988), 141: pp. 4053-4060.
Bernstein, et al.; "Role for a bidentate ribonuclease in the initiation step of RNA interference"; Nature (2001), 409, p. 363.
Better, et al.; "*Escherichia coli* Secretion of an Active Chimeric Antibody Fragment"; Science (1988), 240; pp. 1041-1043.
Boyer, B., et al., "Induction and regulation of epithelial-mesenchymal transitions"; Biochem Pharmacol (2000), 60 (8); pp. 1091-1099.
Bromberg, J., "Stat proteins and oncogenesis"; J Clin Invest (2002), 109 (9); pp. 1139-1142.
Chang,G. D., et al; "Improvement of glycosylation in insect cells with mammalian glycosyltransferases"; Journal of Biotechnology (2003) 102, pp. 61-71.
Christofori, G., et al, "The role of the cell-adhesion molecule E-cadherin as a tumor-suppressor gene"; Trends Biochem Sci 24(2); pp. 73-76, (1999).

(Continued)

Primary Examiner—Robert Landsman
(74) Attorney, Agent, or Firm—Michael P. Morris; Mary-Ellen M. Devlin; Wendy A. Petka

(57) ABSTRACT

The functional characterization of ILEI to be a novel cytokine involved in epithelial/mesenchymal transition and the identification of biologically active ILEI provides the basis for generating ILEI inhibitors, in particular anti-ILEI antibodies, that are useful in the therapy of cancer, fibrosis and COPD.

22 Claims, 29 Drawing Sheets

OTHER PUBLICATIONS

Ciruna, B., et al, "FGF signaling regulates mesoderm cell fate specification and morphogenetic movement at the primitive streak"; Dev. Cell, (2001) 1(1); pp. 37-49.
Coker, R.K., et al, "Localisation of transforming growth factor beta1 and beta3 mRNA transcripts in normal and fibrotic human lung"; Thorax (2001) 56(7); pp. 549-556.
Coussens, L. M., et al., "Inflammation and cancer." Nature (2002) 420 (6917); pp. 860-867.
De Wever, O., et al; "Role of myofibroblasts at the invasion front"; Biol Chem, (2002), 383(1); pp. 55-67.
Dillmann, R. O.; "Perceptions of Herceptin : a monoclonal antibody for the treatment of breast cancer"; Cancer Biother. Radiopharm. (1999) 14; pp. 5-10.
Ding H., et al; "A Mice with Cre recombinase activatable PDGF-C expression" Genesis Feb; (2002) 32 (2); pp. 181-183.
Duband, J.L., et al; "Epithelium-mesenchyme transition during neural crest development"; Acta. Anat., (1995), 154(1); pp. 63-78.
Ellenrieder, V., et al., "Invasion and metastasis in pancreatic cancer." Ann Oncol, (1999), 10 Suppl 4; pp. 46-50.
Emini, E. A., et al; "Induction of Hepatitis A Virus-Neutralizing Antibody by a Virus-Specific Synthetic Peptide"; J Virology (1985), 55, pp. 836-839.
Fidler, I. J., et al, "Biologic diversity in metastatic neoplasms-origins and implications"; Science, (1982) 217; pp. 998-1001.
Fidler, I. J., "The pathogenesis of cancer metastasis: the 'seed and soil' hypothesis revisited"; Nat Rev Cancer (2003), 3(6); pp. 453-458.
Figini, M. et al., "Panning phage antibody libraries on cells: isolation of human Fab fragments against ovarian carcinoma using guided selection"; Cancer Res. (1998) 58; pp. 991-996.
Fire, A. et al., "Potent and specific genetic interference by double-stranded RNA in *Caenorhabditis elegans*" ; Nature (1998), 391; pp. 806-811.
Frey et al., "Epidermal Growth Factor-stimulated intestinal epithelial cell migration requires Src family kinase-dependent p38 MAPK signaling"; J Biol Chem. (2004), 279 (42); pp. 44513-44521.
Joseph, G. et al; "'Peptide Walking' Is a Novel Method for Mapping Functional Domains in Proteins"; Biol Chem.; vol. 270, No. 49, (1995), pp. 29079-29082.
Goding, "Monoclonal Antibodies: Principles and Practice"; Academic Press (1986), pp. 59-103.
Gonzalez-Rothi, R.J.,et al, "Effects of low-yield-cigarette smoke inhalation on rat lung macrophages"; J Toxicol Environ Health, (1986), 17(2-3); pp. 221-228.
Goumenos, D.S., et al., "Apoptosis and myofibroblast expression in human glomerular disease: a possible link with transforming growth factor-beta-1"; Nephron, (2002), 92(2); pp. 287-296.
Grunert, S., et al; "Diverse cellular and molecular mechanisms contribute to epithelial plasticity and metastasis"; Nat Rev Mol Biol (2003) 4(8); pp. 657-665.
Hanahan, D., et al ; "Less is more regularly: metronomic dosing of cytotoxic drugs can target tumor angiogenesis in mice"; J Clin Invest (2000) 105 (8); pp. 1045-1047.
Hanahan, D., et al; "The hallmarks of cancer"; Cell (2000) 100(1); pp. 57-70.
Haseloff J., et al; "Simple RNA enzymes with new and highly specific endoribonuclease activities"; Nature (1988) 334; pp. 585-591.
Hay, E. D.; "An overview of epithelio-mesenchymal transformation"; Acta Anat (Basel) (1995) 154(1); pp. 8-20.
Hay E. D., et al, "Transformations between epithelium and mesenchyme: normal, pathological, and experimentally induced"; Am J Kidney Dis (1995) 26(4); pp. 678-690.
Heider, K., et al; "A Human Homologue of the Rat Metastasis-associated Variant of CD44 Is Expressed in Colorectal Carcinomas and Adenomatous Polyps"; J Cell Biol (1993) 120(1); pp. 227-233
Hellstrom,K. E. et al; "Antibodies for Drug Delivery", Controlled Drug Delivery (2nd Ed.), Robinson et al. (eds.) (1987), pp. 623-653 (Marcel Dekker, Inc.).
Holgate, S.T., "Epithelial damage and response"; Clin Exp Allergy, 30 Suppl (2000) 1; pp. 37-41.

Janda, E. et al; "Ras and TGFBeta cooperatively regulate epithelial cell plasticity and metastasis: dissection of Ras signaling pathways"; J Cell Biol, Jan. 21, 2002, 156 (2); pp. 299-313.
Janda, E., et al; "Oncogenic Ras/Her-2 mediate hyperproliferation of polarized epithelial cells in 3D cultures and rapid tumor growth via the PI3K pathway"; Oncogene (2002), 33; pp. 5148-5159.
Jameson, B.A., et al; "The antigenic index: a noval algorithm for predicting antigenic determinants"; Comput Appl Biosci (1988) 4, pp. 181-186.
Jespers, L. S., et al.; "Guiding the Selection of Human Anitbodies from Phage Display Repertoires to a Single Epitope of an Antigen"; Bio/Technology (1994), 12; pp. 899-903.
Jones, P. T., et al; "Replacing the complementarity-determining regions in a human antibody with those from a mouse"; Nature (1986) 321; pp. 552-525.
Kyte, J., et al; "A simple method for displaying the hydropathic character of a protein"; J. Mol. Biol., (1982), 157, pp. 105-132.
Koehler G., et al; "Continuous cultures of fused cells secreting antibody of predefined specificity"; Nature, (1975), 25; pp. 495-497.
Li, G., et al; "Function and regulation of melanoma-stromal fibroblast interactions: when seeds meet soil"; Oncogene (2003) 22 (20); pp. 3162-3171.
Liu, A. Y., et al; "Chimeric mouse-human IgG1 antibody that can mediate lysis of cancer cells"; Proc. Natl. Acad. Sci. USA (1987) 84; pp. 3439-3443.
Liu, A. Y., et al; "Production of a mouse-human chimeric monoclonal antibody to CD20 with potent Fc-dependent biologic activity"; J. Immunol (1987) 139; pp. 3521-3526.
Lonberg, N. et al; "Human Antibodies from Transgenic Mice"; Int. Rev. Immunol (1995) 13; pp. 65-93.
Markowitz, D, et al; "A Safe Packaging Line for Gene Transfer: Separating Viral Genes on Two Different Plasmids"; J. Virol. (1988) 62(4); pp. 1120-1124.
Martin, M., et al., "Role of stromal myofibroblasts infiltrating colon cancer in tumor invasion"; Pathol Res Pract (1996) 192 (7); pp. 712-717.
McCafferty, J., et al; "Phage antibodies: filamentous phage displaying antibody variable domains"; Nature (1990) 348; pp. 552-554.
McCormick, L.L., Y. Zhang, E. Tootell, and A.C. Gillman, "Anti-TGF-beta treatment prevents skin and lung fibrosis in murine sclerodermatous graft-verus-host disease: a model for human scleroderma," J. Immunol., (1999), 163(10); 5693-5699.
Mikulits, W., B. Pradet-Balade, et al., "Isolation of transationally controlled mRNAs by differential screening." Faseb J, (2000), 14(11): 1641-52.
Moriggl, R., C. Kristofic, et al., "Activation of STAT proteins and cytokine genes in human Th1 and Th2 cells generated in the absence of IL-12 and IL-4". J Immunol, (1998), 160(7): 3385-92.
Morrison; "Transfectomas Provide Novel Chimeric Anitbodies" Science, (1985), 229:1202-1207.
Nishimura, et al.; "Recombinant human-mouse chimeric monoclonal anitbody specific for common acute lymphocytic leukemia antigen" Canc. Res., (1987), 47:999-1005.
Niu, G., Wright, K. L., et al., Constitutive STAT3 activity up-regulates VEGF expression and tumor angiogenesis.: Oncogene, (2002), 21(3): 2000-8.
Niwa, H., et al.; "Self-renewal of pluripotent embryonic stem cells is mediated via activation of STAT3" Genes Dev., Jul. 1, 1998, 12(13): 2048-60.
Oft, M., Peli, J. et al., "TGF-beta1 and Ha-Ras collaborate in modulating the phenotypic plasticity and invasiveness of epithelial tumor cells." Genes Dev, (1996), 10(19): 2462-77.
Oft, M., Heider, K. H., et al., TGFbeta signaling is necessary for carcinoma cell invasiveness and mestastasis. Curr Biol., (1998), 8(23): 1243-52.
Oi, et al.; "Chimeric Antibodies" Bio/Techniques, (1986), 4:214.
Ozkaynak, et al., Phase I study of chimeric human/murine anti-ganglioside G(D2) monoclonal antibody (ch14.18) with granulocyte-macrophage colony—stimulating factor in children with neuroblastoma immediately after hematopoietic stem-cell transplantation: a Children's Cancer Group, (2000).

Paulus, W., WT AL., "Self-contained, tetracycline-regulated retroviral vector system for gene delivery to mammalian cells." J Virol, (1996), 70(1): 62-7.

Peterson, R.E. and McClay, D.R., "Primary mesenchyme cell patterning during the early stages following ingression." Dev. Biol., (2003), 254(1): 68-78.

Plieth, et al.; "Evidence that fibroblasts derive from epithelium during tissue fibrosis" J Clin Invest, Aug. 2002, 110(3): 341-50.

Press, et al., "Immunotherapy of Non-Hodgkin's lymphomas Hematology." Am Soc. Hematol. Educ. Program, (2001), 221-40.

Ramaswamy, S., K.N. Ross., et al., "A molecular signature of metastasis in primary solid tumors." Nat Genet, (2003), 33(1): 49-54.

Reichmann, et al.; "Activation of an inducible c-FosER fusion protein causes loss of epithelial polarity and triggers epithelial-fibroblastoid cell conversion" Cell, Dec. 24, 1992, 71(7): 1103-16.

Shaw, et al.; "Mouse/Human Chimeric Antibodies to a Tumor-Associated Antigen: Biologic Activity of the Four Human IgG Subclasses" J Natl. Cancer Inst., (1988), 80:1553-1559.

Sun, et al.; "Chimeric anitbody with human constant regions and mouse variable regions directed against carcinoma-associated antigen 17-1A" Proc. Natl. Acad. Sci. USA, (1987), 84:214-218.

Sun, D., C.R. Vanderburg, G.S. Odierna, and E.D. Hay, "TGFbeta3 promotes transformation of chicken palate medial edge epithelium to mesenchyme in vitro." Development, (1998), 125(1): 95-105.

Takeda, K., Noguchi, K., et al., "Targeted disruption of the mouse STAT3 gene leads to early embryonic lethality." Proc. Natl. Acad Sci USA, (1997), 94(8): 3801-4.

Thiery, J.P., "Cell adhesion in development: a complex signaling network." Curr Opin Genet Dev, (2003), 13(4): 365-71.

Thorpe, et al., "The Preparation and Cytotoxic Properties of Antibody-Toxin Conjugates", Immunol. Rev., (1982), 62:119-58.

Thorpe, "Antibody Carriers of Cytotoxic Agents in Cancer Therapy : A Review", in Monclonal Antibodies '84: Biological and Clinical Applications, Pinchera et al. (eds.), (1985), pp. 475-506.

Uananue and Benacerraf, Textbook of Immunology, 2nd Edition, William & Wilkins, (1984), p. 218.

Valerio, et al.; "Synthesis of peptide analogues using the multipin peptide synthesis method"Anal Biochem. Aug. 15, 1991; 197(1): 168-77.

Verhoeyan, et al.; "Reshaping human antibodies: grafting an antilysozyme activity" Science, (1988), 239-1534.

Vicovac, L. and Aplin, J.D., "Epithelial-mesencyhmal transition during trophoblast differentiation." Acta Anat., (1996), 156(3): 202-216.

Gruvberger, et al.; "Expression profiling to predict outcome in breast cancer: the influence of sample selection" Breast Cancer Res. 2003, 5(1): 23-6. Epub Oct. 11, 2002.

Wang, Q., Y. Wang, D.M. Hyde, P.J. Gotwals, V.E. Koteliansky, S.T. Ryan, and S.N. Giri, "Reduction of bleomycin induced lung fibrosis by transforming growth factor beta soluable receptor in hamsters," Thorax, (1999), 54(9); 805-812.

Wang, et al., "Domain-domain associations in cystic fibrosis transmembrane conductance regulator" Am J Physical Cell Physiolm, (2002), 282: C1170-C1180, 2002.

Ward, et al., "Phase I clinical trial of the chimeric monoclonal antbody (c30.6) in patients with metastastic colorectal cancer" Clin. Cancer Res., (2000), 6:4674-83.

Wood, et al.; "The synthesis and in vivo assembly of functional antibodies in yeast" Nature, (1985), 314:446-449.

Yamashita, S., Miyagi, C., et al., "STAT3 Controls Cell Movements during Zebrafish Gastrulation." Dev Cell (2002), 2(3): 363-75.

Yang, J. and Y. Liu, "Blockage of tubular epithelial to myofibroblast transition by hepatocyte growth factor prevents renal interstitial fibrosis." J. Am. Soc. Nephrol., (2002), 13(1): 96-107.

Yu and Sato; "MAP Kinases, Phosphatidylinositol 3-Kinase, and p70 S6 Kinase Mediate the Mitogenic Response of Human Endothelial Cells to Vascular Endothelial Growth Factor" J Cell Physiol, Feb. 1999, 178(2): 235-46.

Yu et al.; "RNA interference by expression of short-interfacing RNSs and hairpin RNAs in mammalian cells" Proc Natl Acad Sci USA, Apr. 30, 2002, 99(9):6047-52.

Zhang, H.Y., M. Gharaee-Kermani, K. Zhang, S. Karmiol, and S.H. Phan., "Lung fibroblast alpha-smooth muscle actin expession and contractile phenotype in bleomycin-induced pulmonary fibrosis," Am. J. Pathol., (1996), 148(2): 527-537.

* cited by examiner

Fig. 1a

| cell line | *in vivo* tumors | *in vivo* metastases |
|---|---|---|
| EpH4 | - | - |
| EpBcl2 | - | - |
| EpC40 | + | - |
| CKR2 | + | - |
| EpS35 | + | + |
| EpRas | + | + |
| CT26 | + | + | tumor progression ↓

Fig. 1b

| cell pair | 1 | | 2 | | 3 | | 4 | | |
|---|---|---|---|---|---|---|---|---|---|
| | EpRas | | EpS35R | | CKR2 | CT26 | EpC40R | | EpH4 |
| ex-tumour (XT) | − | + | − | + | − | − | − | + | − |
| EMT | − | + | − | + | − | + | − | − | − |
| ILEI polys. RNA (fold change) | 1 | 4.1 | 1 | 2.1 | 1 | 3.3 | 1 | −2.5 | nd |

24K −    ILEI

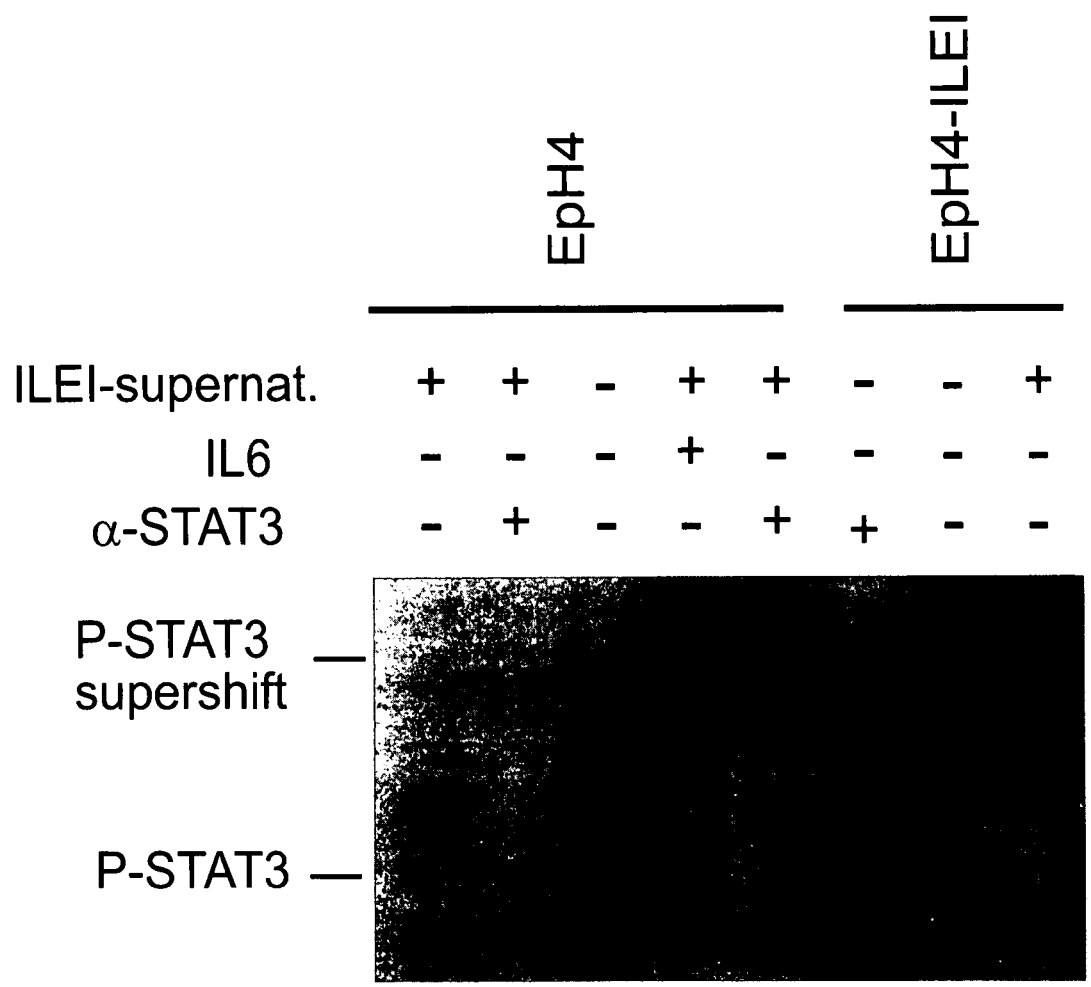

EpH4 / control     EpH4 / ILEI epithelial phenotype     invasive phenotype

EpRasXT  EpRasXT-siRNA-ILEI clone

EpRas / anti ILEI rabbit-IgG

EpRas / rabbit-IgG

SEQUENCE LISTING

```
<160> NUMBER OF SEQ ID NOS: 17

<210> SEQ ID NO 1
<211> LENGTH: 2475
<212> TYPE: DNA
<213> ORGANISM: Homo sapiens
<220> FEATURE:
<221> NAME/KEY: 5'UTR
<222> LOCATION: (1)..(167)
<220> FEATURE:
<221> NAME/KEY: CDS
<222> LOCATION: (168)..(851)
<220> FEATURE:
<221> NAME/KEY: 3'UTR
<222> LOCATION: (852)..(2475)

<400> SEQUENCE: 1
ccggaggagt ccgagaggaa gcggaggcgc gagctggagg cggcggctcc cgtcggcctc        60
cggcaggact gagcgctggg aggccggaag gcgggcgcgc acggcggaga ggcgggcggg       120
aggccggagc atattaatga aaagtgccat aaactgaaaa accaaac atg agg gta        176
                                                    Met Arg Val
                                                      1 gca ggt gct gca aag ttg gtg gta gct gtg gca gtg ttt tta ctg aca        224
Ala Gly Ala Ala Lys Leu Val Val Ala Val Ala Val Phe Leu Leu Thr
  5                  10                  15 ttt tat gtt att tct caa gta ttt gaa ata aaa atg gat gca agt tta        272
Phe Tyr Val Ile Ser Gln Val Phe Glu Ile Lys Met Asp Ala Ser Leu
 20                  25                  30                  35 gga aat cta ttt gca aga tca gca ttg gac aca gct gca cgt tct aca        320
Gly Asn Leu Phe Ala Arg Ser Ala Leu Asp Thr Ala Ala Arg Ser Thr
                 40                  45                  50 aag cct ccc aga tat aag tgt ggg atc tca aaa gct tgc cct gag aag        368
Lys Pro Pro Arg Tyr Lys Cys Gly Ile Ser Lys Ala Cys Pro Glu Lys
             55                  60                  65 cat ttt gct ttt aaa atg gca agt gga gca gcc aac gtg gtg gga ccc        416
His Phe Ala Phe Lys Met Ala Ser Gly Ala Ala Asn Val Val Gly Pro
         70                  75                  80 aaa atc tgc ctg gaa gat aat gtt tta atg agt ggt gtt aag aat aat        464
Lys Ile Cys Leu Glu Asp Asn Val Leu Met Ser Gly Val Lys Asn Asn
     85                  90                  95
```

```
gtt gga aga ggg atc aat gtt gcc ttg gca aat gga aaa aca gga gaa      512
Val Gly Arg Gly Ile Asn Val Ala Leu Ala Asn Gly Lys Thr Gly Glu
100                 105                 110                 115 gta tta gac act aaa tat ttt gac atg tgg gga gga gat gtg gca cca      560
Val Leu Asp Thr Lys Tyr Phe Asp Met Trp Gly Gly Asp Val Ala Pro
            120                 125                 130 ttt att gag ttt ctg aag gcc ata caa gat gga aca ata gtt tta atg      608
Phe Ile Glu Phe Leu Lys Ala Ile Gln Asp Gly Thr Ile Val Leu Met
                135                 140                 145 gga aca tac gat gat gga gca acc aaa ctc aat gat gag gca cgg cgg      656
Gly Thr Tyr Asp Asp Gly Ala Thr Lys Leu Asn Asp Glu Ala Arg Arg
            150                 155                 160 ctc att gct gat ttg ggg agc aca tct att act aat ctt ggt ttt aga      704
Leu Ile Ala Asp Leu Gly Ser Thr Ser Ile Thr Asn Leu Gly Phe Arg
165                 170                 175 gac aac tgg gtc ttc tgt ggt ggg aag ggc att aag aca aaa agc cct      752
Asp Asn Trp Val Phe Cys Gly Gly Lys Gly Ile Lys Thr Lys Ser Pro
180                 185                 190                 195 ttt gaa cag cac ata aag aac aat aag gat aca aac aaa tat gaa gga      800
Phe Glu Gln His Ile Lys Asn Asn Lys Asp Thr Asn Lys Tyr Glu Gly
                200                 205                 210 tgg cct gaa gtt gta gaa atg gaa gga tgc atc ccc cag aag caa gac      848
Trp Pro Glu Val Val Glu Met Glu Gly Cys Ile Pro Gln Lys Gln Asp
            215                 220                 225 taa tggaaatgtg gagagaattg aagaaagcgc actttcactc ttaatgggag           901
agctataaat ggcagagcta tgtgtaaata ttttaagagc atgcagccat cttggtgtgt    961
gcatgagtat tgtctctttt gatatcagga ttatttattg ctaacgtaaa tagatagcat    1021
tgtaaataat catcacaatg atcaaatcac tgaaccatgt ctccgcacat ttccctaaaa    1081
gtacaatgtt tagactgcta tggtaataca tattttaaat tctaaaagca tacacaatgt    1141
gtaactgaat ggtttgtgaa aaatatattg atatatatac tagttgctat gaaaatatca    1201
tggaataata gggattttag ggtggatact ttattttctt ttatgtttct atatgttgcg    1261
ttgtgatgac attatctttt aaattaaaaa gagatttggc tagttgtgtg tgtaatgtta    1321
ctttacagtc cgactctcct gatgtacctc ttttcatgat cttttttcttt ccttcccaag   1381 aaactgagga atgtttaata tgaaaacata catcggatat gtgaaaagca caacaaaatt    1441
cttaatgtac acagtaaaaa agtaaatata taaatgtaga tggcatttag gaccacagct    1501
tgctggattt gtgttagcta tgggaataac ttgattttgt ataagctatt tagagtgagg    1561
ctggaggtgg cagcttcaca gaactggaga accaggccaa gtcccctccc caacctaatt    1621
aggtcattca ggacagctaa gtcagtatat ttagagcaat actagcatac gttttctta    1681 attgttatca gcattgacca agtggtttgg aaggaggcat gctttaatat cacaataatt    1741
ttgatttgta aaccaagaaa ttaatcctgt gtttatctaa cttcataata gcaattattg    1801
cccgaagcta tagtggcata tttacaaaag ttcttattac tgggcggact gataacattt    1861
aaaaaataat tgtgtttgac cccaaatgac tttatacccca attctacata aaaatataga   1921
agatctatct ttttttgtta ccttcagatg ttcactaaat aactcagttt ttaagcagaa    1981
gttttcaggg cattaaatat atgttgtgta tgaagtatct caaactggaa cataaattta    2041
gtgatcaaac tgccattcac agtgtaaggc agcacttaaa tttcgaacct aaagtttaga    2101
tgcattgtat aaaaaaacct aaaagcagta tctgttattt agctgtaaac caagttggaa    2161
gctattcgga taatttctta aatattgatg aactttggag tactgttcct tccttcaaac    2221
tgaatgtaat taattcatga ataaatgcac cttatatgtt taaacaatct tgtatactt     2281
```

-continued

```
ttgggatttt tggtgcttat atgctaaatc acattcagca tgtgtatttt gacatttaaa    2341
atacttccct caattctgta aattaaaaga atagttattt tacagttcca gggattgtga    2401
aataaatgtt gcagttttt aaataatga aataaatac tcttggtttt gctttgtgaa       2461
aaaaaaaaaa aaaa                                                      2475
```

<210> SEQ ID NO 2
<211> LENGTH: 227
<212> TYPE: PRT
<213> ORGANISM: Homo sapiens

<400> SEQUENCE: 2

```
Met Arg Val Ala Gly Ala Ala Lys Leu Val Ala Val Ala Val Phe
1               5                   10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
            100                 105                 110

Thr Gly Glu Val Leu Asp Thr Lys Tyr Phe Asp Met Trp Gly Gly Asp
        115                 120                 125

Val Ala Pro Phe Ile Glu Phe Leu Lys Ala Ile Gln Asp Gly Thr Ile
    130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
            180                 185                 190

Lys Ser Pro Phe Glu Gln His Ile Lys Asn Asn Lys Asp Thr Asn Lys
        195                 200                 205

Tyr Glu Gly Trp Pro Glu Val Val Glu Met Glu Gly Cys Ile Pro Gln
    210                 215                 220

Lys Gln Asp
225
```

<210> SEQ ID NO 3
<211> LENGTH: 687
<212> TYPE: DNA
<213> ORGANISM: Mus musculus
<220> FEATURE:
<221> NAME/KEY: misc_feature
<222> LOCATION: (1)..(2)
<220> FEATURE:
<221> NAME/KEY: CDS
<222> LOCATION: (3)..(686)
<220> FEATURE:
<221> NAME/KEY: misc_feature
<222> LOCATION: (687)..(687)

<400> SEQUENCE: 3

```
aa atg agg gta gca gga gct gca aag ttg gta gtg gcc gtg gca gta                    47
   Met Arg Val Ala Gly Ala Ala Lys Leu Val Val Ala Val Ala Val
   1               5                  10                  15 ttc tta ctg acc ttc tat gtt att tct caa gta ttt gaa att aaa atg                   95
Phe Leu Leu Thr Phe Tyr Val Ile Ser Gln Val Phe Glu Ile Lys Met
                    20                  25                  30 gat gca agt tta gga aat cta ttt gct cga tcc gcg ctg gac tca gcc                  143
Asp Ala Ser Leu Gly Asn Leu Phe Ala Arg Ser Ala Leu Asp Ser Ala
                35                  40                  45 att cgt tct acg aaa cct ccg agg tac aag tgt ggg atc tca aag gcg                  191
Ile Arg Ser Thr Lys Pro Pro Arg Tyr Lys Cys Gly Ile Ser Lys Ala
            50                  55                  60 tgc cca gag aag cat ttt gct ttt aag atg gct agt gga gca gcc aat                  239
Cys Pro Glu Lys His Phe Ala Phe Lys Met Ala Ser Gly Ala Ala Asn
65                  70                  75 gtc gtg gga ccc aag atc tgc ctg gag gac aat gtt ttg atg agt ggt                  287
Val Val Gly Pro Lys Ile Cys Leu Glu Asp Asn Val Leu Met Ser Gly
80                  85                  90                  95 gtg aag aat aat gtc gga aga gga atc aat att gcc ttg gta aat ggg                  335
Val Lys Asn Asn Val Gly Arg Gly Ile Asn Ile Ala Leu Val Asn Gly
                    100                 105                 110 aaa aca ggg gaa gta ata gac acc aaa ttt ttt gac atg tgg gga gga                  383
Lys Thr Gly Glu Val Ile Asp Thr Lys Phe Phe Asp Met Trp Gly Gly
                115                 120                 125 gat gtg gca cca ttc att gag ttt ttg aag acc ata caa gac gga aca                  431
Asp Val Ala Pro Phe Ile Glu Phe Leu Lys Thr Ile Gln Asp Gly Thr
            130                 135                 140 gta gtg cta atg gct aca tac gat gat gga gca acc aaa ctc acg gat                  479
Val Val Leu Met Ala Thr Tyr Asp Asp Gly Ala Thr Lys Leu Thr Asp
            145                 150                 155 gag gca cgg cgg ctc att gct gaa ctg ggc agc act tcg atc acc agt                  527
Glu Ala Arg Arg Leu Ile Ala Glu Leu Gly Ser Thr Ser Ile Thr Ser
160                 165                 170                 175 ctt ggt ttc cga gat aac tgg gtc ttc tgt ggt ggg aag ggc att aag                  575
Leu Gly Phe Arg Asp Asn Trp Val Phe Cys Gly Gly Lys Gly Ile Lys
                    180                 185                 190 aca aag agt ccc ttt gaa cag cac ata aag aac aat aag gaa acg aac                  623
Thr Lys Ser Pro Phe Glu Gln His Ile Lys Asn Asn Lys Glu Thr Asn
                195                 200                 205 aag tac gag gga tgg cct gag gtg gtg gag atg gaa gga tgt atc ccc                  671
Lys Tyr Glu Gly Trp Pro Glu Val Val Glu Met Glu Gly Cys Ile Pro
            210                 215                 220 cag aag caa gac tga c                                                            687
Gln Lys Gln Asp
        225

<210> SEQ ID NO 4
<211> LENGTH: 227
<212> TYPE: PRT
<213> ORGANISM: Mus musculus

<400> SEQUENCE: 4

Met Arg Val Ala Gly Ala Ala Lys Leu Val Val Ala Val Ala Val Phe
1               5                   10                  15

Leu Leu Thr Phe Tyr Val Ile Ser Gln Val Phe Glu Ile Lys Met Asp
                    20                  25                  30

Ala Ser Leu Gly Asn Leu Phe Ala Arg Ser Ala Leu Asp Ser Ala Ile
                35                  40                  45

Arg Ser Thr Lys Pro Pro Arg Tyr Lys Cys Gly Ile Ser Lys Ala Cys
            50                  55                  60
```

```
Pro Glu Lys His Phe Ala Phe Lys Met Ala Ser Gly Ala Ala Asn Val
 65                  70                  75                  80

Val Gly Pro Lys Ile Cys Leu Glu Asp Asn Val Leu Met Ser Gly Val
                 85                  90                  95

Lys Asn Asn Val Gly Arg Gly Ile Asn Ile Ala Leu Val Asn Gly Lys
            100                 105                 110

Thr Gly Glu Val Ile Asp Thr Lys Phe Phe Asp Met Trp Gly Gly Asp
        115                 120                 125

Val Ala Pro Phe Ile Glu Phe Leu Lys Thr Ile Gln Asp Gly Thr Val
    130                 135                 140

Val Leu Met Ala Thr Tyr Asp Asp Gly Ala Thr Lys Leu Thr Asp Glu
145                 150                 155                 160

Ala Arg Arg Leu Ile Ala Glu Leu Gly Ser Thr Ser Ile Thr Ser Leu
                165                 170                 175

Gly Phe Arg Asp Asn Trp Val Phe Cys Gly Gly Lys Gly Ile Lys Thr
            180                 185                 190

Lys Ser Pro Phe Glu Gln His Ile Lys Asn Asn Lys Glu Thr Asn Lys
        195                 200                 205

Tyr Glu Gly Trp Pro Glu Val Val Glu Met Glu Gly Cys Ile Pro Gln
    210                 215                 220

Lys Gln Asp
225

<210> SEQ ID NO 5
<211> LENGTH: 49
<212> TYPE: DNA
<213> ORGANISM: Artificial
<220> FEATURE:
<223> OTHER INFORMATION: Description of Artificial Sequence: Primer

<400> SEQUENCE: 5
ggggacaagt ttgtacaaaa aagcaggcta aatgagggta gcaggagct                49

<210> SEQ ID NO 6
<211> LENGTH: 53
<212> TYPE: DNA
<213> ORGANISM: Artificial
<220> FEATURE:
<223> OTHER INFORMATION: Description of Artificial Sequence: Primer

<400> SEQUENCE: 6
ggggaccact ttgtacaaga aagctgggtg tcagtcttgc ttctggggga tac           53

<210> SEQ ID NO 7
<211> LENGTH: 50
<212> TYPE: DNA
<213> ORGANISM: Artificial
<220> FEATURE:
<223> OTHER INFORMATION: Description of Artificial Sequence: Primer

<400> SEQUENCE: 7
ggggaccact ttgtacaaga aagctgggtg gtcttgcttc tgggggatac                50

<210> SEQ ID NO 8
<211> LENGTH: 22
<212> TYPE: PRT
<213> ORGANISM: Mus musculus

<400> SEQUENCE: 8

Val Lys Asn Asn Val Gly Arg Gly Ile Asn Ile Ala Leu Val Asn Gly
```

```
1               5                   10                  15
Lys Thr Gly Glu Val Ile
            20

<210> SEQ ID NO 9
<211> LENGTH: 23
<212> TYPE: PRT
<213> ORGANISM: Mus musculus

<400> SEQUENCE: 9

Gly Ile Lys Thr Lys Ser Pro Phe Glu Gln His Ile Lys Asn Asn Lys
1               5                   10                  15

Glu Thr Asn Lys Tyr Glu Gly
            20

<210> SEQ ID NO 10
<211> LENGTH: 23
<212> TYPE: PRT
<213> ORGANISM: Homo sapiens

<400> SEQUENCE: 10

Gly Ile Lys Thr Lys Ser Pro Phe Glu Gln His Ile Lys Asn Asn Lys
1               5                   10                  15

Asp Thr Asn Lys Tyr Glu Gly
            20

<210> SEQ ID NO 11
<211> LENGTH: 73
<212> TYPE: DNA
<213> ORGANISM: Artificial
<220> FEATURE:
<223> OTHER INFORMATION: Description of Artificial Sequence: Primer

<400> SEQUENCE: 11
taagaatact gccacggcca ctaccaacga agcttggttg gtagtggtcg tggtagtgtt      60
cttattgttt ttt                                                        73

<210> SEQ ID NO 12
<211> LENGTH: 81
<212> TYPE: DNA
<213> ORGANISM: Artificial
<220> FEATURE:
<223> OTHER INFORMATION: Description of Artificial Sequence: Primer

<400> SEQUENCE: 12
ttaaaaaaaa caataagaac actaccacga ccactaccaa ccaagcttcg ttggtagtgg      60
ccgtggcagt attcttaccg g                                               81

<210> SEQ ID NO 13
<211> LENGTH: 381
<212> TYPE: DNA
<213> ORGANISM: Artificial
<220> FEATURE:
<223> OTHER INFORMATION: Description of Artificial Sequence: Vector
      Sequence

<400> SEQUENCE: 13
gatccgacgc cgccatctct aggcccgcgc cggccccctc gcacagactt gtgggagaag      60
ctcggctact cccctgcccc ggttaatttg catataatat ttcctagtaa ctatagaggc     120
ttaatgtgcg ataaaagaca gataatctgt tctttttaat actagctaca ttttacatga     180
taggcttgga tttctataag agatacaaat actaaattat tattttaaaa aacagcacaa     240
```

-continued

```
aaggaaactc accctaactg taaagtaatt gtgtgttttg agactataaa tatcccttgg      300
agaaaagcct tgtttgggcc cccctcgag gtcgacggta tcgataagct tgatatcgaa      360
ttcctgcagc ccgggggatc c                                                381

<210> SEQ ID NO 14
<211> LENGTH: 49
<212> TYPE: DNA
<213> ORGANISM: Artificial
<220> FEATURE:
<223> OTHER INFORMATION: Description of Artificial Sequence: Primer

<400> SEQUENCE: 14
ggggacaagt ttgtacaaaa aagcaggctg atccgacgcc gccatctct                  49

<210> SEQ ID NO 15
<211> LENGTH: 46
<212> TYPE: DNA
<213> ORGANISM: Artificial
<220> FEATURE:
<223> OTHER INFORMATION: Description of Artificial Sequence: Primer

<400> SEQUENCE: 15
ggggaccact ttgtacaaga aagctgggtg gatccccgg gctgca                      46

<210> SEQ ID NO 16
<211> LENGTH: 20
<212> TYPE: DNA
<213> ORGANISM: Artificial
<220> FEATURE:
<223> OTHER INFORMATION: Description of Artificial Sequence: Primer

<400> SEQUENCE: 16
aaatgagggt agcaggagct                                                  20

<210> SEQ ID NO 17
<211> LENGTH: 19
<212> TYPE: DNA
<213> ORGANISM: Artificial
<220> FEATURE:
<223> OTHER INFORMATION: Description of Artificial Sequence: Primer

<400> SEQUENCE: 17
aacattgtcc tccaggcag                                                   19
```

ANTIBODIES TO INTERLEUKIN-LIKE EPITHELIAL-MESENCHYMAL TRANSITION INDUCER (ILEI)

RELATED APPLICATION

This application claims priority to International Application No. PCT/EP2004/009790, filed Sep. 2, 2004, which claims priority to European Patent Application No. 03 019 551.5, filed Sep. 2, 2003, the contents of which are incorporated herein by reference in their entirety.

FIELD OF THE INVENTION

The present invention relates to the therapy of diseases that are associated with epithelial/mesenchymal transition, in particular to the prevention and treatment of cancer and to the therapy of fibrotic diseases and chronic obstructive pulmonary disease (COPD).

In a simplified way, cancer may be described as a chronic disease due to the involvement of many pro-inflammatory cytokines that can attract and activate leukocytes, which leads to a complex tissue remodeling process within the tumor microenvironment (for review see Coussens, 2002). With the support of tumor stroma and infiltrating cells, cancer is able to progress from a single affected cell to a local tumor and finally to metastases, which are largely responsible for the death of the tumor patient. So far, different mechanisms for tumor initiation and progression have been detected. These mechanisms are dependent on the tissue origin of the tumor cell and the strategy of oncogenic transformation, i.e. the way in which cells can overcome the usually precisely controlled mechanisms of DNA repair, cell growth and apoptosis (Hanahan et al., 2000). After the step of neoplastic transformation, growth and progression of tumor cells require production of autocrine growth factors or the ability to respond to external stimuli such as hormones or growth and differentiation factors. Among the cytokines secreted by cancer cells of epithelial origin are transforming growth factor α (TGFα), transforming growth factor β (TGFβ), platelet-derived growth factors A and B, epidermal growth factor (EGF) and basic fibroblast growth factor (bFGF). These cytokines may act in an autocrine or paracrine manner to stimulate tumor growth (Ellenrieder, 1999). Due to the permanently changing microenvironment of the host organism, the metastatic process of cancer can be seen as a late stage of a multistep interaction between tumor cells and the tumor environment.

Essential steps in the development of metastasis are: (I): proliferation (neoplastic transformation), angiogenesis and protection from apoptosis; (II): detachment of tumor cells from the primary lesion and invasion of the local stroma; (III): embolization of tumor cells or cell aggregates into the circulation; (IV): adherence of tumor cells to the subendothelial basement membrane (extravasation) and (V): invasion into the organ parenchyma. In response to autocrine and/or paracrine growth factors, single invaded tumor cells are able to proliferate and induce angiogenesis to establish secondary tumor lesions (metastases), which themselves may form additional metastases. The pathogenesis of metastasis is complex and consists of multiple sequential steps that are regulated by the interaction between tumor cells and the microenvironment of the host. Therefore, metastasis can be viewed as a highly selective competition, favoring the survival of specific tumor cells that preexist within the clonally heterogeneous primary tumor (Fidler and Hart, 2002).

For this multistep progression of metastasis, relatively few genetic and/or epigenetic changes have been characterized that contribute to local invasion and metastasis (Christofori and Semb, 1999; Hanahan and Weinberg, 2000; Ramaswamy et al., 2003). During the past five years, evidence has accumulated that epithelial to mesenchymal transition (EMT) represents an in vitro correlate of late-stage tumor progression including tissue invasion and aspects of metastasis (Boyer et al., 2000; Peterson et al., 2003; Thiery, 2003). An epithelial-mesenchymal transition (EMT) characterizes the progression of many carcinomas and it is linked to the acquisition of an invasive phenotype.

During EMT, cells lose epithelial polarity and acquire a spindle-shaped, highly motile fibroblastoid phenotype. This includes loss or redistribution of tight and adherens junction proteins and the ability to pass through the basement membrane (Hay, 1995 a, b; Oft et al., 1996). EMT is regulated by an increasingly complex pattern of signaling pathways and occurs also during embryonic development (Grunert et al., 2003; Hay, 1995 a, b; Thiery, 2003) and during fibrosis in different tissues (Plieth et al., 2002).

It has been an object of the present invention to further elucidate EMT by identifying genes involved in this process in order to provide novel therapies for disorders in which EMT is involved, in particular to interfere with the metastatic potential of tumor cells and for the treatment of fibrosis, and therapies of COPD.

BRIEF DESCRIPTION OF THE FIGURES

FIG. 1(a)-(d): Characterization of ILEI: translational upregulation during EMT and tumor progression and production of recombinant ILEI.

DESCRIPTION OF INVENTION

Figure 1C:
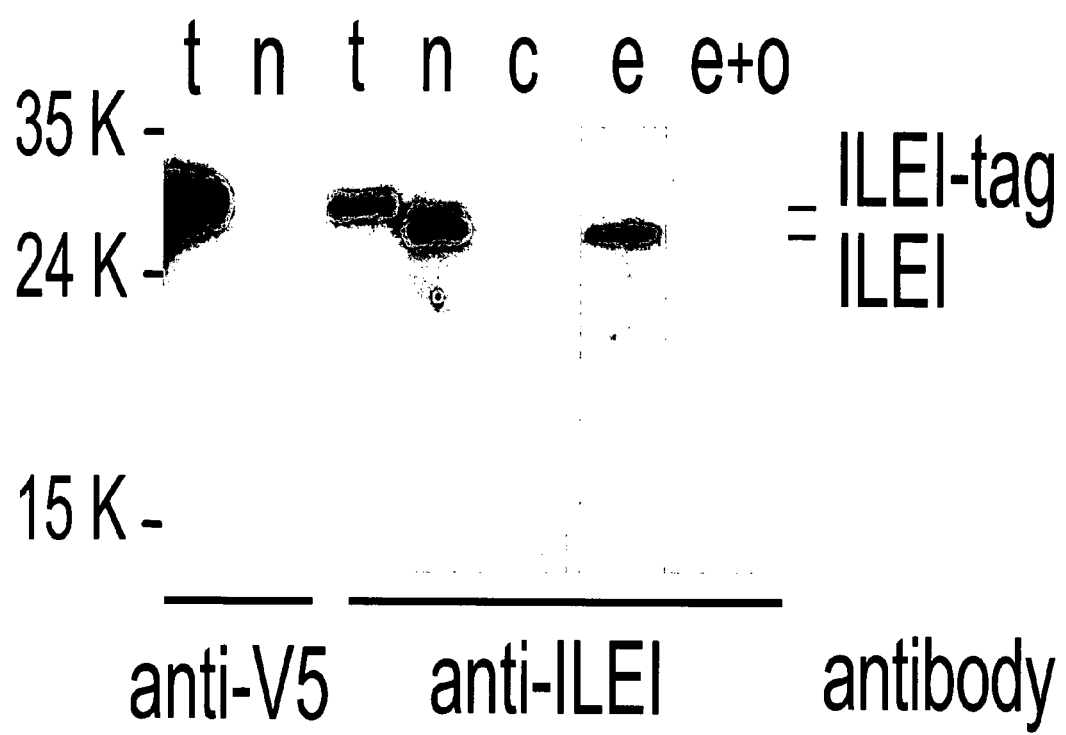

To solve the problem underlying the invention, the microarray technology was used, which has been proven to allow genome wide screening for de-regulated genes (van't Veer et al., 2003). This methodology is useful for massive parallel investigation of gene expression, e.g. in tumor samples from patients or in EMT cell models designed in vitro.

The investigation was based on a microarray approach using polysome-bound RNA of well characterized, clonally related, murine cell pairs. The cell lines were described in detail (Oft et al., 1996; Janda et al., 2002 a). Each cell pair represents a specific stage of epithelial plasticity that correlates with a respective tumor stage.

The basic cell line used in this approach is a spontaneously immortalized epithelial mammary gland cell line (EpH4), which was compared on polysomal RNA expression level with EpH4 cells that overexpress the Ras oncogene or mutated V12Ras proteins. Each mutated Ras was selected such that it activates a defined signaling pathway out of the broad Ras-signaling network in order to discover the relevance of the respective pathway for EMT. Among the selected cells were Ep_C40 (mutated V12RasC40, mainly PI3K signaling), Ep_S35 (mutated V12RasS35, mainly MAPK signaling) (Janda et al., 2002 a,b), and also Ep_BCL2 (apoptosis-protected), Ep_FOS_ER (estrogen-inducible FOS). Translated RNA was compared either before injection in the mouse fat pad, and after isolation and cultivation of corresponding tumor cells (XT cells) before and after expressing of BCL2 or before and after induction of estrogen induced FOS expression in Ep_FOS/ER cells.

The above-described cell model represents three stages of epithelial plasticity, i.e.

a) fully polarized cells, b) not polarized, scattered cells that still express epithelial markers and c) mesenchymal cells that underwent EMT (Grunert et al., 2003).

One of the proteins that was identified in the above-described investigation due to its ability to induce EMT, is a protein designated ILEI (Interleukin-Like EMT Inducer.)

Human ILEI (originally designated "FAM3C", Accession No: NM_014888) was recently published to represent a member of a novel gene family (Fam3). The nucleotide and amino acid sequence of human ILEI are shown in SEQ ID NO:1 and SEQ ID NO:2, respectively.

The Fam3 family was identified using structure-based methods to search for four-helix-bundle cytokines (Zhu et al., 2002). ILEI shows no sequence homology to other cytokines or other known genes, and so far no functional data have been published. One of the family members, Fam3B, was shown to be specifically and highly expressed in the islets of Langerhans of the endocrine pancreas. Although its precise physiological role is still unclear, FAM3B has been suggested to be a negative regulator of the β cell function.

The similarity of ILEI (Fam3C) with the other members of the Fam3 family has been reported as follows: ILEI—Fam3A: 47.4% similarity; ILEI—Fam3B: 32.5% similarity; ILEI—Fam3D: 50.2% similarity.

In experiments of the invention, surprisingly, evidence for a contribution of ILEI in epithelial-mesenchymal transition (EMT) was gathered. Overexpression of ILEI was shown to induce EMT in non-tumorigenic mammary epithelial cells (EpH4) and renders these cells tumorigenic in nude mice. In a related cell line (EpRasC40, bearing a Ras mutant which does not induce EMT), which is tumorigenic in nude mice but unable to metastasize, ILEI strongly enhances tumor growth and promotes lung metastases formation upon tail vein injection. ILEI also induced enhanced cell motility and migration in respective assays, both after stable expression and after addition of purified or partially purified recombinant ILEI protein to the cells. ILEI seems to indirectly activate STAT3 tyrosine phosphorylation and DNA binding.

Furthermore, RNA interference (RNAi) of ILEI was performed in cells after EMT (Ras-XT, i.e. Ras transformed EpH4 cells isolated as mesenchymal cells from tumors, causing frequent metastases after tail vein injection) by expression of siRNA (small interfering RNA) via suitable retroviral vectors. Knockdown of ILEI in Ras-XT cells reverted the cells to an epithelial morphology and strongly reduced metastases formation. Taken together, these data suggest that ILEI plays a role in tumorigenesis.

Thus, the present invention is based on the functional characterization of the cytokine-like protein ILEI, which was first identified by the inventors due to its upregulation on the level of polysome-bound RNA and on the level of secreted protein after Ras/TGFβ-induced epithelial to mesenchymal transition in the murine mammary gland cell system. Further investigations showed that ILEI is involved in tumorigenesis.

As downstream signaling molecule of ILEI, STAT3 was identified. STAT3 signaling is involved in a variety of tumor-related functions including proliferation, ES cell-renewal (Niwa et al., 1998), EMT, migration (Yamashita et al., 2002) and apoptosis protection (Bromberg, 2002).

Furthermore, it was shown that ILEI RNA is detectable with PCR during mouse development at day 7.5 and later, which correlates with the time point of STAT3 knock-out embryo degeneration during day 6.5-8.5 (Takeda et al., 1997). None of the known STAT3 activators can account for this early embryonic function.

Stable expression of ILEI was shown to be sufficient to induce EMT in EpH4, EpRas and EpS35. Furthermore, in vivo analysis with nude mice revealed that stable expression of ILEI protein at low levels induced tumorigenicity in spontaneously immortalized EpH4 murine mammary gland cells. This finding was highly surprising because normal EpH4 cells, when injected into the mammary gland region of female nude mice, are encapsulated by mouse cells and have never been shown to develop tumors. EpH4_ILEI cells appear, by a so far unknown mechanism, to be refractory to this defence by the endogenous mouse cells. It may be assumed that besides inducing EMT, secreted ILEI protein induces local tissue remodeling which increases the chance for each tumor cell to survive in its modified micro environment and thus significantly supports tumor growth.

An additional in vivo evidence for the tumor-promoting function of ILEI is the finding that stable expression of secreted ILEI significantly promotes tumor growth of EpC40_ILEI cells compared to EpC40. Tumors derived from EpC40_ILEI cells showed a mesenchymal morphology of the GFP positive tumor cell fraction. In a next step, it is determined if the GFP negative cells are tumor cells that lost ILEI-IRES-GFP expression or if they are host cells, either infiltrated fibroblasts or epithelial cells that underwent EMT induced by the secretion of ILEI by the EpC40_LEI cells. EpC40_ILEI tumors exhibited a more heterogenous morphology as compared to their smaller-sized EpC40 counterparts because distinct areas within these tumors showed GFP negative cells with epithelial structures expressing E-cadherin on the cell surface. Possibly these murine epithelial cells infiltrate the tumor which leads then to mechanical stabilization of the unusual high portion of hollow structures containing the GFP positive cell fraction.

Strikingly, stable expression of ILEI induced metastatic potential in non-tumorigenic and non-metastatic EpH4 epithelial cells and potentiated the formation of lung metastasis in nude mice when these cells were injected in the blood stream by tail vein injection.

In addition to the tumor-promoting functions of STAT3 described above, the migratory function of ILEI may be an important advantage for the development of metastases by giving mechanical support for the evasion of tumor cells into and out of the blood stream. Beside the "seed and soil theory", according to which metastases evade microvessels of specific organs mainly by specific interactions of the metastasising cell with the epithelial cell, a second theory supports a random evasion of metastases from the blood stream. According to this theory, cell motility can even more directly enhance invasion of new organs by metastases through blood vessel barrier. This theory explains organ specificity of metastases by later selection steps in the host organ (Fidler, 2003). As studies revealed, the establishment of metastasis is the final outcome of a multistep processes such as tumor growth, angiogenesis, tumor cell detachment and invasion of extracellular matrix. Each step is essential for tumor cell survival and establishment of secondary lesions and is regulated by interactions of tumor cells with host microenvironment. The understanding of the molecular mechanisms and the regulation of each of these steps may contribute to the development of more effective strategies for diagnosis and treatment.

The findings of the present invention show the importance of the ILEI protein for migration and EMT in the development of metastases. Possibly, the strong pro-metastatic potential of ILEI is due to a combination of its enhanced migration ability and the ability for tissue remodeling in the host organ.

ILEI may be important for tissue remodeling primarily at the tumor boundary, where mesenchymal cells, for example myofibroblasts are detectable in various tumors (De Wever, 2002; Martin, 1996) or during remodeling processes within the tumor, like angiogenesis (Li et al., 2003). Inside most observed tumors, cells revert to an epithelial phenotype and loose their migratory activity (Oft et al., 1996). It seems that this reversion was blocked in the ILEI-induced tumor because of the constitutive expression of ILEI in the EpH4_ILEI derivatives. Therefore mesenchymal to epithelial transition (MET) is strongly decreased and most cells keep in a mesenchymal shape within the whole tumor mass and form a spongy like structure. As described above, only a small portion of most in vivo tumor cells is mesenchymal.

The role of ILEI in cancer was confirmed by immunostaining of ILEI in patient samples; the role of ILEI in tissue remodeling during fibrotic diseases can be confirmed in a similar manner by analyzing fibrotic tissue.

The inventors also investigated whether ILEI may be involved in COPD: Since long-term smoking is the main factor for the development of COPD, the inventors tested whether cigarette smoke exposure on rats influences the expression of ILEI. To determine ILEI's role in COPD, the effect of cigarette smoke on rat lungs was analysed by comparison of lung samples from "smoked" and no-smoke rats. After 6 weeks of smoke exposure, an enhanced number of ILEI positive cells was detected.

The present invention is based on the finding that human ILEI is a target molecule in the treatment of diseases in which EMT is involved, in particular in the treatment of cancer and fibrosis, and of COPD.

Furthermore, the invention is based on the identification of a novel, biologically active ILEI protein:

Analysis of the published ILEI amino acid sequence (corresponding to SEQ ID NO:2 or SEQ ID NO:4, respectively), for patterns or domains reveals that the sequence contains a secretion signal. As predicted by bioinformatics programs, the cleavage site would be expected to lie be between amino acids Ser 24 and Gin 25. In the experiments of the invention ILEI with the predicted N-terminus did not have biological activity. It was found that the biologically active ILEI protein starts at an amino acid between position 41 and 44.

In a first aspect, the present invention relates to a biologically active ILEI polypeptide with an amino acid sequence starting at a position selected from amino acids 41 to 44 and terminating at position 227 of SEQ ID NO:2 or SEQ ID NO:4, respectively, and to a polynucleotide molecule with a sequence encoding such ILEI polypeptide, or polypeptides or polynucleotide molecules with a sequence sufficiently identical to these sequences and variants and fragments thereof.

In a preferred embodiment, the biologically active ILEI polypeptide starts at position 42 of the amino acid sequence of SEQ ID NO:2 or SEQ ID NO:4, respectively.

In the meaning of the present invention, the term "biologically active" (or "functional") in the context of ILEI is defined as the ability of ILEI to enhance motility of epithelial cells, as it can be determined by assaying epithelial cells for their invasiveness, upon addition of ILEI, into various matrices, e.g. a collagen matrix, or by time-lapse microscopy or by subjecting epithelial cells to a so-called "wound closure assay" (as e.g. described Frey et al., 2004).

In addition to the ability to enhance cell motility, which is the minimum requirement for ILEI to be considered as biologically active, the ILEI protein of the invention has, in a preferred embodiment, the ability to induce, upon addition to epithelial cells, a scattered morphology of such cells and/or to induce epithelial to mesenchymal transition (EMT). A scattered phenotype can be determined by microscopical analysis: epithelial cells that have acquired a scattered morphology manifest themselves as cells with a fibroblast-like shape. Alternatively, a scattered phenotype can be determined by assaying for delocalization of epithelial markers like E-cadherin. EMT can be determined by microscopic analysis of cells for a mesenchymal morphology or by assaying for loss or downregulation, combined with delocalization, of epithelial markers, combined with assaying for mesenchymal markers like vimentin.

The term "sufficiently identical" refers to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common functional activity. Variant nucleic acid molecules and polypeptides substantially identical to the nucleotide and amino acid sequences set forth in the sequence listings are encompassed by the present invention. A sequence substantially similar has preferably at least 80% identity, more preferably at least ca. 90% identity and most preferably at least 95% identity on the amino acid level or encodes an amino acid sequence with such identity.

More specifically, the invention encompasses a polynucleotide that hybridizes with a polynucleotide of the sequence shown in SEQ ID NO:1 or SEQ ID NO:3 under stringent conditions and that comprises or contains a sequence encoding a biologically active ILEI polypeptide, and a polypeptide encoded by such polynucleotide that has the biological activity of ILEI as defined herein.

By "stringent hybridization conditions" as used herein is meant overnight incubation at 42° C. in a solution comprising: 50% formamide, 5×SSC (1×SSC=150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C., or equivalent conditions.

In the following, the term "ILEI" encompasses the above-defined ILEI molecules, including the novel ILEI protein having the biological activity of naturally occurring ILEI.

A fragment is defined as having at least 8 amino acids of the ILEI polypeptide sequence or a DNA molecule encoding at least 8 amino acids.

In initial experiments of the invention, recombinant murine ILEI was obtained by expression of ILEI cDNA from baculovirus/insect cell expression systems The employed expression constructs took into account the predicted cleavage site and were thus designed to express the tentative mature product starting with Gln 25. However, the recombinant ILEI as obtained with the chosen expression system failed to show activity in functional assays. This prompted the inventors to the possibility that the recombinant protein as obtained in insect cells in the chosen experimental setting (i.e. the expression construct and the culture conditions) may not have folded into its native conformation, may lack potential post-translational modifications or may be processed differently than predicted from its published sequence.

Therefore, given that supernatants of COS7 cells transiently expressing ILEI (see Material and Methods j) had shown biological activity in functional assays (see Example 4), in an approach to obtain biologically active ILEI, the inventors produced recombinant ILEI by expressing it in mammalian cells (HEK 293; human embryonic kidney cells) and purifying it. The obtained recombinant purified ILEI showed biological activity in functional assays, as defined above.

Analysis of the obtained recombinant ILEI revealed that the N-terminus differs from the cleavage site as predicted from the published sequence. The protein, when expressed in mammalian cells, was found to start at an amino acid between position 41 and 44, mostly at amino acid 42, whereas the predicted N-terminus of mature ILEI is at amino acid 25.

Furthermore, upon analysis of purified ILEI from 293 cells by mass spectrometry, the inventors observed a peak pattern that is most likely due to glycosylation.

Detailed analysis of this pattern suggests that the protein might be modified by an oligosaccharide composed of N-actyineuraminic acid, N-acetylhexosamine, and hexose modules. The conducted analysis strongly suggests that the glycosylation site is Thr 51 (O-glycosylation).

Thus, based on the analysis of the correctly processed recombinant product, as obtained in the experiments of the invention in mammalian cells, the structure of ILEI differs in at least two aspects from the one of predicted from SEQ ID NO:2 or SEQ ID NO:4, respectively:

Firstly, the N-terminus of the mature protein is 17 amino acids further C-terminal as compared to the predicted cleavage site.

Secondly, the protein is glycosylated.

Given the high homology between murine and human ILEI, the cleavage site as well as the potential O-glycosylation site found in murine ILEI are also present in human ILEI.

Therefore, in a further embodiment, the present invention relates to a biologically active human and murine ILEI polypeptide having the amino acid sequence starting at a position selected from amino acids 41 to 44 and terminating at position 227 of SEQ ID NO:2 or SEQ ID NO:4, which is glycosylated.

Cleavage between amino acid 41 and 42 (or in vicinity of this cleavage site) is not presumed to affect the predicted disulfid formation of ILEI. However, it removes part of the predicted alpha helix (helix 1), which should prevent the formation of helix 1. As a consequence, the assignment of ILEI to the family of four-helix-bundle cytokines, as suggested by Zhu et al., 2002, may not be correct.

To enhance the functional blocking activity of anti-ILEI IgG, rabbit sera were generated against the biologically active ILEI protein of the invention, the sequence of which is different from the one expected from the published sequence, as described above.

The initial immunization had been done with ILEI protein obtained by expressing cDNA encoding a protein with the predicted N-terminus in insect cells. In this protein (starting with Gln 25), important peptide epitopes of ILEI (conformational epitopes) may be missing or different because of different protein folding due to the different N-terminus. A similar effect on relevant ILEI epitopes is expected to be due to the detected glycosylation of ILEI. As protein glycosylation is not identical in insect cells compared to mammalian cells, immunization of an animal with the recombinant protein as obtained in insect cells could lead to a reduced number of anti-ILEI antibodies.

In a further embodiment, the invention relates to methods for producing biologically active ILEI. Preferably, biologically active ILEI is obtained by expression in mammalian cells, in which secreted and correctly processed ILEI can be obtained by using established expression systems as routinely used in the industry, e.g. for COS7 cells, HEK 293 cells or CHO cells.

Alternatively, bioactive ILEI may be obtained from baculovirus/insect cell expression systems by expressing a vector containing a construct starting at an N-terminus as determined according to the present invention, e.g. at Ser 42, Arg 41, or Leu 44. Alternatively, vectors encoding a secretion signal in front of the mature protein may be used. Glycosylation of the product may be controlled by co-expression of glycosyltransferases (as described by e.g. Chang et al., 2003). N-terminal or C-terminal purification tags with or without protease cleavage sites (e.g. TEV, thrombin, Factor Xa, enterokinase, etc.) may be added to facilitate purification.

A similar strategy may be employed for obtaining recombinant mature ILEI from yeast (e.g. *Saccharomyces* or *Pichia* strains) intracellularly or via secretion into the medium by expression of ILEI as a precursor protein carrying the appropriate secretion signal that will be processed by the host's signal peptidases.

Correctly processed ILEI may also be obtained by expression of ILEI in *E. coli*, either intracellularly or by targeting the protein to the periplasmic space with the aid of appropriate targeting sequences.

In a further aspect, the invention relates to the use of a) a human ILEI DNA molecule of SEQ ID NO: 1 or a murine ILEI DNA molecule of SEQ ID NO:3 or a variant encoding a polypeptide with at least about 80% identity with a human ILEI polypeptide of SEQ ID NO:2 or a murine ILEI polypeptide of SEQ ID NO:4, or a fragment thereof or a complement thereto, or of b) a human ILEI polypeptide of SEQ ID NO:2 or a murine ILEI polypeptide of SEQ ID NO:4 or a variant with at least about 80% identity or a fragment thereof, or of c) a biologically active ILEI polypeptide d) a DNA molecule encoding biologically active ILEI polypeptide, for the generation of an inhibitor of the biological function of murine or human ILEI.

In a further embodiment, the present invention relates to the use of an above-defined ILEI polypeptide (or a fragment thereof) or a DNA molecule encoding it, as immunogen for generating an anti-ILEI antibody.

In a preferred aspect, the present invention relates to anti-ILEI antibodies, anti-ILEI antibody fragments and anti-ILEI antibody conjugates. Antibodies include, but are not limited to, polyclonal, monoclonal, humanized, bispecific, and heteroconjugate antibodies.

ILEI or an ILEI peptide, or alternatively ILEI DNA, can be used as an immunogen to generate anti-ILEI antibodies using standard techniques for polyclonal and monoclonal antibody preparation.

Preferably, the full-length biologically active ILEI protein of the invention starting at a position selected from amino acid 41 to 44 and terminating at position 227 of SEQ ID NO:2 or SEQ ID NO:4, most preferably starting at position 42, or a fusion protein thereof or, alternatively, antigenic ILEI peptide fragments derived therefrom are used as immunogens.

Alternatively, a DNA molecule encoding ILEI (usually the full-length protein of SEQ ID NO:2 or SEQ ID NO:4) or an ILEI peptide can be employed by means of DNA immunization.

An antigenic ILEI-derived peptide comprises at least 8, preferably 10, 15, 20, or 30 amino acid residues of the amino acid sequence shown in SEQ ID NO:2, preferably from the sequence from position 42 to 227 of SEQ ID NO:2 and encompasses an epitope of ILEI such that an antibody raised against the peptide forms a specific immune complex with ILEI. By way of example, the (antigenic) human ILEI peptide GIKTKSPFEQHIKNNK<u>D</u>TNKYEG (SEQ ID NO:10; the underlined position represents difference from the murine ILEI sequence, which has an E in this position) that comprises amino acids 189 to 211 can be used.

Additional immunogenic fragments and peptides derived from ILEI can be determined by so-called prediction algorithms such as for example the surface probability blot (Emini et al., 1985), the hydrophobicity blot (Kyte and Doolittle, 1982) and the antigenic index (Jameson and Wolf, 1988). Computer programs based on these algorithms are readily available.

With regard to producing anti-ILEI antibodies, numerous methods are available:

Polyclonal anti-ILEI antibodies can be prepared by immunizing a suitable animal (e.g. rabbit, goat, mouse, or other mammal) with an ILEI immunogen. The antibody titer in the immunized subject can be monitored by standard techniques, such as with an enzyme linked immunosorbent assay (ELISA). Polyclonal anti-ILEI antibodies are particularly useful for conducting experiments that show an anti-tumor effect, e.g. a direct effect by anti-proliferative or pro-apoptotic activity or an indirect effect (in the case of blocking membrane-associated ILEI) by antibody-dependent cellular cytotoxicity (ADCC) or complement-dependent cytotoxicity (CDC).

Monoclonal antibodies are highly specific by being directed against a single antigenic site (epitope). While polyclonal antibody preparations include different antibodies directed against different epitopes, a monoclonal antibody is directed against a single epitope.

Monoclonal anti-ILEI antibodies are antibodies obtained from a population of substantially homogeneous antibodies, independent of any particular method by which the antibodies were generated. For example, anti-ILEI monoclonal antibodies may be obtained by the hybridoma method that was first described by Koehler and Milstein (1975), or may be made by recombinant DNA methods such as described in U.S. Pat. No. 4,816,567.

A monoclonal anti-ILEI antibody can also be obtained by screening a recombinant combinatorial immunoglobulin library (e.g. an antibody phage display library) with an ILEI protein to isolate molecules that bind the ILEI protein, as described, for example, in McCafferty et al. (1990). Kits for generating and screening phage display libraries are commercially available, e.g. from Pharmacia and Stratagene.

As mentioned above, monoclonal antibodies may be prepared using hybridoma technology, such as the method first described by Koehler and Milstein (1975) and by Goding (1986).

In brief, in a hybridoma method, an appropriate host animal, e.g. a mouse, is immunized to elicit lymphocytes that produce antibodies binding to the immunogen.

The lymphocytes obtained from the host animal (or lymphocytes obtained by immunization in vitro) are then fused with an immortalized cell line to form hybridoma cells. Immortalized cell lines are usually transformed mammalian cells, particularly myeloma cells, e.g. rat, mouse or human myeloma cell lines. The hybridoma cells are then cultured in a suitable culture medium that inhibits the growth or survival of the unfused, immortalized cells. The culture medium is then tested for the presence of anti-ILEI monoclonal antibodies according to established methods.

The obtained clones may be subcloned and grown by standard methods. The monoclonal antibodies may be isolated or purified from the culture medium by conventional immunoglobulin purification procedures.

Monoclonal anti-ILEI antibodies may also be made by recombinant DNA methods, such as those described in U.S. Pat. No. 4,816,567. DNA encoding the monoclonal anti-ILEI antibodies can be isolated and sequenced by routinely used procedures, e.g. by using oligonucleotide probes that bind to sequences encoding the heavy and light chains of murine antibodies. As a source of such DNA, hybridomas may be used. The DNA isolated is then inserted into expression vectors, which are transfected into host cells, e.g. COS cells or CHO cells to obtain the monoclonal antibodies in the recombinant host cells. The DNA may be modified, e.g. by replacing the sequences encoding the heavy and light chain constant domains of the murine sequences by the corresponding human sequences, as described in U.S. Pat. No. 4,816,567.

In another embodiment, the anti-ILEI antibodies may be monovalent antibodies. Methods for preparing monovalent antibodies are well known in the art, e.g. recombinant expression of immunoglobulin light chain and modified heavy chain. The heavy chain may be truncated at any point in the Fc region to prevent heavy chain crosslinking. Alternatively, the cysteine residues may be deleted or substituted with other amino acid residues.

To obtain antibody fragments, e.g. Fab fragments, digestion can be accomplished by means of routine techniques, e.g. using papain. Examples of papain digestion are described in WO 94/29348 and U.S. Pat. No. 4,342,566. Papain digestion of antibodies typically produces two identical antigen binding fragments, so-called Fab fragments, each with a single antigen binding site, and a residual Fc fragment. Pepsin treatment yields an F(ab')$_2$ fragment that has two antigen combining sites and is still capable of cross-linking the antigen.

The Fab fragments obtained by digestion of the antibody also contain the constant domains of the light chain and the first constant domain (CH$_1$) of the heavy chain. Fab' fragments differ from Fab fragments in that they contain additional residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them.

In another aspect, the present invention relates to recombinant anti-ILEI antibodies, such as chimeric and humanized monoclonal antibodies, comprising both human and non-human portions.

Humanized forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues which are found neither in the recipient antibody nor in the imported CDR or framework sequences. In general, the humanized antibody will comprise substantially all of at least one, usually two, variable domains, in which all or substantially all of the CDR regions correspond to those of a non-human immunoglobulin and all or substantially all of the FR regions are those of a human immunoglobulin consensus sequence.

Chimeric and humanized monoclonal anti-ILEI antibodies can be produced by recombinant DNA techniques known in the art, for example using methods described in the patent documents WO 86/101533; WO 87/02671; EP 184,187; EP 171,496; EP 125,023; EP 173,494; U.S. Pat. No. 4,816,567; U.S. Pat. No. 5,225,539; EP 125,023; Better et al. (1988); Liu et al. (1987); Sun et al. (1987); Nishimura et al. (1987); Wood et al. (1985); Shaw et al. (1988); Morrison (1985); Oi et al. (1986); Jones et al. (1986); Verhoeyan et al (1988); and Beidler et al. (1988).

In another embodiment, the invention provides completely human anti-ILEI antibodies, which are particularly desirable for therapeutic treatment of human patients. Such antibodies can be produced using transgenic mice that are incapable of expressing endogenous immunoglobulin heavy and light chains genes, but can express human heavy and light chain genes, e.g. as described by Lonberg and Huszar (1995); U.S. Pat. No. 5,625,126; U.S. Pat. No. 5,633,425; U.S. Pat. No. 5,569,825; U.S. Pat. No. 5,661,016; and U.S. Pat. No. 5,545,806.

Completely human antibodies that recognize a selected epitope can also be generated using a technique referred to as "guided selection", which is based on the display of repertoires of human antibody fragments on filamentous phages and selection by binding of the phage to the antigen. In this approach, a selected non-human monoclonal antibody, e.g. a murine antibody, is used to guide the selection of a completely human antibody recognizing the same epitope. This technology was described e.g. by Jespers et al. (1994) and Figini et al. (1998), who generated a human antibody against a cell surface antigen that is overexpressed in many human ovarian carcinomas. The guiding template was provided by the light chain of a mouse monoclonal antibody which was paired with repertoires of human heavy chains displayed on phages.

Antibodies from all subclasses may be used, preferred anti-ILEI antibodies belong to the subclasse IgG, preferably the anti-ILEI antibody is an IgG1 or IgG4 antibody.

In a further aspect, the invention relates to conjugates of anti-ILEI antibody (or a fragment thereof) and a therapeutic moiety or a radioactive metal ion. Examples of therapeutic moieties (e.g. cytotoxic or anti-mitotic agents or anti-metabolites or antibiotics), are taxanes, emetine, mitomycin, etoposide, tenoposide, vincristine, vinblastine, colchicin, doxorubicin, daunorubicin, dihydroxy anthracin dione, mitoxantrone, mithramycin, methotrexate, 6-mercaptopurine, 6-thioguanine, cytarabine, 5-fluorouracil, decarbazine, mechlorethamine, melphalan, carmustine (BSNU), lomustine (CCNU), cyclothosphamide, busulfan, dibromomannitol, streptozotocin, mitomycin C, cis-dichlorodiamine platinum (II) (DDP) cisplatin, daunorubicin and doxorubicin, bleomycin, mithramycin, anthramycin (AMC), vincristine, vinblastine, maytansine, and analogs or homologs thereof.

Techniques for conjugating a therapeutic moiety to an anti-ILEI antibody are well known, see, e.g. Amon et al. 1985; Hellstrom et al. (1987); Thorpe (1985); Pinchera et al. (1985); Baldwin et al. (1985) and Thorpe et al. (1982). Alternatively, an anti-ILEI antibody can be conjugated to a second antibody, e.g. an anti-CD3 antibody (in order to target the antibodies to T cells) to form an antibody heteroconjugate as described by Segal in U.S. Pat. No. 4,676,980.

Anti-ILEI antibody conjugates may be useful for the therapy of human diseases as defined herein, in particular for the therapy of cancers, in which ILEI is bound to the membrane of the tumor cells. Evidence for a membrane-associated form of ILEI can be obtained from the immunohistochemistry experiment described in Example 11, FIG. 8 A).

In a further aspect, the present invention relates to a pharmaceutical composition comprising, as the active ingredient, an inhibitor of the biological function of ILEI (an "ILEI inhibitor").

In a preferred aspect, the inhibitor of the biological function of ILEI is an anti-ILEI antibody (fragment) or an anti-ILEI antibody conjugate.

Pharmaceutical compositions of the invention containing inhibitors of ILEI, in particular anti-ILEI antibodies, fragments and conjugates that selectively bind ILEI and ILEI fragments, are useful for the treatment of disorders in which ILEI is involved as an inducer and/or promoter of EMT, in particular for the treatment of cancer, e.g. by treating and preventing metastasis, and fibrotic diseases, as well as COPD. Antibodies of virtually any type can be used provided they bind ILEI and exert the desired therapeutic effect, e.g. anti-tumor effect, as described above.

Anti-proliferative activity of an ILEI inhibitor, e.g. an anti-ILEI antibody, can be assessed by standard methods, e.g. by determining the DNA content of treated cells by FACS analysis after DNA stain with propidium iodide. The pro-apoptotic activity cells can be assessed via determination of apoptosis markers (e.g. CaspGLOW™ Fluorescein Active Caspase staining kit) and subsequent FACS analysis.

The ability of a particular anti-ILEI antibody to mediate lysis of tumor cells, e.g. in the case of membrane-bound ILEI, by complement activation and/or ADCC can also be assayed by standard methods: The tumor cells are grown and labeled in vivo; the antibody is added to the tumor cell culture in combination with either serum complement or immune cells which may be activated by the antigen antibody complexes. Cytolysis of the target tumor cells is detected by the release of label from the lysed cells.

An antibody that shows anti-tumor activity, e.g. via an antiproliferative or pro-apoptotic activity or by activating complement or mediating ADCC in the in vitro test, can then be used therapeutically.

Furthermore, the pharmaceutical composition of the invention is useful for the treatment of fibrosis, e.g. lung and kidney fibrosis, or for COPD.

During early development, EMT-like processes occur at several stages; they require the cooperation of TGFβ or related factors such as bone morphogenetic proteins (BMPs) with RTKs (Duband et al., 1995; Beddington et al., 1999; Ciruna and Rossant; 2001; Vicovac and Aplin, 1996; Sun et al., 1998). Importantly, TGFβ and receptor tyrosine kinase signaling also seem to cooperate in chronic inflammatory diseases such as lung and kidney fibrosis, chronic obstructive pulmonary disease (COPD) and chronic asthma (Goumenos et al., 2002; Holgate et al., 2000; Bauer and Schuppan, 2001), leading to collagen deposition and myofibroblast proliferation (Yang and Liu, 2002; Zhang et al., 1996). Fibrotic changes may not only represent (abnormal) fibroblast differentiation, but also transdifferentiation of epithelial cells into myofibroblasts, e.g. transdifferentiation of epithelial cell precursors of lung alveoli or bronchi into myofibroblast-like cells. The requirement of strong inducers of epithelial plasticity such as TGFβ and epidermal growth factor (EGF) or platelet-derived growth factor (PDGF) in fibrosis has been shown in animal models for lung fibrosis and COPD (Coker et al., 2001; McCormick et al., 1999; Wang et al., 1999); the process of EMT was detected during the progression of different fibrotic tissues (Plieth et al., 2002).

Since there is increasing evidence that EMT plays a crucial role in chronic, inflammatory lung, liver and kidney diseases, which involve gradual organ destruction by fibrosis, i.e. the massive accumulation of collagen matrix and proliferation of so-called myofibroblasts, inhibitors of ILEI, in particular anti-ILEI antibodies, which are inhibitors of EMT, are useful for the therapy of such diseases and for treatment of chronic obstructive pulmonary disease (COPD) or chronic asthma.

To confirm the role of ILEI in fibrotic diseases and COPD and thus the usefulness of ILEI inhibitors, e.g. anti-ILEI antibodies, in the therapy of such diseases, cell types and cellular composition in fibrotic lesions induced in animal models for lung fibrosis and COPD can be analysed. To this end, for example, frozen sections of normal and diseased lungs can be subjected to in situ hybridization and/or immunofluorescent staining for epithelial markers such as basal cytokeratins (cytokeratins 8 and 18) which persist in epithelial cells after dedifferentiation/EMT, combined with analysis for mesenchymal markers like vimentin, or collagen typeVI α1. The occurrence of double-positive cells in fibrotic lesions will strongly support an epithelial origin of the fibrotic cells, which can also be analysed for a myofibroblast phenotype by staining for smooth muscle α-actin (α-SMA), and, importantly, for expression of ILEI. Similar studies can be carried out in a skin fibrosis model (involving subcutaneous injection of Bleomycin), to find out whether some or all of the fibrotic skin cells are of keratinocyte progenitor origin (as likely for skin cancer progression).

To investigate the effect of ILEI function or to assess the efficacy of ILEI inhibitors in smoked rat lungs (Gonzalez-Rothi and Harris, 1986) or animal models for fibrosis, functional inhibiting anti-ILEI antibodies or other ILEI inhibitory molecules can be delivered by intratracheal/nasal application of lyophilized antibody or inhibitory peptides to the animals and the effect of the inhibitors tested.

When used in cancer therapy, the anti-ILEI antibodies (or antibody fragments or conjugates) of the invention are administered to the patient in therapeutically effective amounts that eliminate or reduce the patient's tumor/metastasis burden. They will normally be administered parenterally, preferably intravenously or subcutaneously. The dose and dosage regimen will depend upon the nature of the cancer (primary or metastatic), the site to which the antibodies are to be directed, the characteristics of the particular immunotoxin (in the case that an antibody conjugate is used), e.g. its therapeutic index, the patient, and the patient's history. The amount of antibody administered will typically be in the range of about 0.1 to about 30 mg/kg of the patient's body weight.

For parenteral administration, the anti-ILEI antibody (or fragment or conjugate) can be formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Non-aqueous vehicles such as fixed oils and ethyl oleate may also be used. Liposomes may be used as carriers. The vehicle may contain minor amounts of additives such as substances that enhance isotonicity and chemical stability, e.g. buffers and preservatives. The antibodies may typically be formulated in such vehicles at concentrations of about 1 mg/ml to 10 mg/ml.

To select an anti-ILEI antibody for its ability to block the function of ILEI and to thus block the tumor promoting function of ILEI and are effective in human therapy, xenotransplants of human tumors into nude mice can be used. Such experiments can be done according to standard methods, e.g. by transplanting human tumor cells, which may be derived from a cell line or from a primary tumor, subcutaneously or intravenously into immunodeficient mice, e.g. SCID or nude mice.

With regard to cancer, ILEI inhibitory molecules are particularly useful for, but not limited to, the therapy of carcinomas, e.g. for treating adenocarcinomas of the lung, breast, prostate, colon, esophagus or stomach, or for the therapy of squamous cell carcinomas like HNSCC (head and neck squamous cell carcinoma), tumors of the esophagus, lung and cervix.

For therapy of patients with disorders of the lung, like fibrosis or COPD, ILEI inhibitory molecules can be delivered preferentially by oral application or nasal spray or powder formulation or aerosol for inhalation. The routes for administration (delivery) in patients include, but are not limited to, one or more of: oral (e.g. as a tablet, capsule, or as an ingestable solution), topical, mucosal (e.g. as a nasal spray or powder or aerosol for inhalation), nasal, parenteral (e.g. by an injectable form), gastrointestinal, intraspinal, intraperitoneal, intramuscular, intravenous, intradermal, intratracheal, intracerebroventricular, intracerebral, subcutaneous, ophthalmic (including intravitreal or intracameral), transdermal, rectal, buccal, vaginal, epidural, sublingual. ILEI inhibitory molecules are preferentially delivered by oral application or nasal spray or powder formulation or aerosol for inhalation.

In another embodiment, the pharmaceutical composition comprises more than one ILEI inhibitor as the active ingredient. In this case, it is to be understood that not all of the of the active ingredients need be administered at the same time or by the same route. Likewise, if the composition comprises more than one active ILEI inhibitors, then these inhibitors may be administered by different routes.

Apart from being applied in therapy, anti-ILEI antibodies can be used diagnostically, e.g. to monitor ILEI levels in blood or tissues as part of a clinical testing procedure, e.g. to, for example, determine the efficacy of a given treatment regimen. Detection can be facilitated by coupling the anti-ILEI antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin. Examples of suitable radioactive labels include $^{125}I$, $^{131}I$, $^{35}S$, or $^{3}H$ Furthermore, an anti-ILEI antibody can be used to detect ILEI protein (e.g. in a cellular lysate or cell supernatant) in order to evaluate the abundance and pattern of expression of the ILEI protein, e.g. to determine the protein localization in different human/mouse tumors and normal tissues to confirm the relevance of endogenous ILEI for tumorigenesis.

Furthermore, an anti-ILEI antibody (e.g. monoclonal antibody) is useful for isolating the ILEI protein, e.g. by affinity chromatography or immunoprecipitation. An anti-ILEI antibody can facilitate the purification of natural and recombinantly produced ILEI.

In a further aspect, the ILEI inhibitor is an ILEI antisense molecule. Thus, the present invention encompasses ILEI antisense nucleic acid molecules, i.e. molecules that are complementary to a sense nucleic acid encoding ILEI, e.g. complementary to the coding strand of the double-stranded ILEI cDNA molecule (SEQ ID NO:1 or SEQ ID NO:3), or complementary to the ILEI mRNA. The antisense nucleic acid can be complementary to an entire ILEI coding strand, or, preferably, to only a portion thereof, e.g. all or part of the ILEI coding region (or open reading frame).

Given the coding-strand sequence encoding the ILEI protein (SEQ ID NO:1 or SEQ ID NO:3), antisense nucleic acids of the invention can be designed according to the rules of Watson and Crick base pairing. For example, the antisense oligonucleotide can be complementary to the region surrounding the translation start site of the ILEI mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

Usually, an antisense oligonucleotide is chemically synthesized using naturally occurring nucleotides or nucleotides that have been modified to increase the biological stability of the molecules or to increase the physical stability of the duplex formed between the antisense and sense nucleic acids, e.g. phosphorothioate derivatives and acridine-substituted nucleotides. Alternatively, the antisense nucleic acid can be produced using an expression vector into which a nucleic acid has been subcloned in an antisense orientation (thus, RNA transcribed from the inserted nucleic acid is of an antisense orientation to the ILEI nucleic acid).

The antisense nucleic acid molecules of the invention are typically administered to a subject or generated in situ such that they hybridize with or bind to cellular mRNA and/or genomic DNA encoding the ILEI protein to thereby inhibit expression of ILEI, e.g. by inhibiting transcription and/or translation. An example of a route of administration of antisense nucleic acid molecules of the invention includes direct injection at a tissue site. Alternatively, antisense nucleic acid molecules can be modified to target selected cells and then administered systemically. The antisense nucleic acid molecules can also be delivered to cells using vectors. To achieve sufficient intracellular concentrations of the antisense molecules, vector constructs in which the antisense nucleic acid molecule is placed under the control of a strong pol II or pol III promoter are useful.

With regard to ILEI antisense molecules, their use as inhibitors of the function of ILEI, in particular as active ingredients in pharmaceutical compositions for human therapy, the criteria described above for anti-ILEI antibodies apply.

In a further aspect, the invention also encompasses, as ILEI inhibitors, ILEI ribozymes. Ribozymes are catalytic RNA molecules with ribonuclease activity that are capable of cleaving a single-stranded nucleic acid, such as an mRNA, to which they have a complementary region. Ribozymes (e.g. hammerhead ribozymes as described by Haselhoff and Gerlach, 1988) can be used to catalytically cleave ILEI mRNA transcripts to thereby inhibit translation of ILEI mRNA. A ribozyme having specificity for an ILEI encoding nucleic acid can be designed based upon the nucleotide sequence of ILEI cDNA (SEQ ID NO:1 or 3), as described in U.S. Pat. No. 4,987,071 and U.S. Pat. No. 5,116,742. Alternatively, ILEI mRNA can be used to select a catalytic RNA having a specific ribonuclease activity from a pool of RNA molecules, see e.g. Bartel and Szostak (1993). Administration of an ILEI ribozyme may be done as described above for antisense molecules.

With regard to ILEI ribozymes, their use as inhibitors of the function of ILEI, in particular as active ingredients in pharmaceutical compositions for human therapy, the criteria described above for anti-ILEI antibodies apply.

In a further aspect, the invention also encompasses, as ILEI inhibitors, short interfering RNA (siRNA) molecules that down regulate expression of an ILEI gene by RNA interference ("ILEI siRNA").

RNA interference refers to the process of sequence-specific post transcriptional gene silencing in animals mediated by short interfering RNAs (siRNA) (Fire et al., 1998). siRNA molecules are short pieces of dsRNA obtained by processing of the dsRNA by Dicer, a ribonuclease III enzyme (Bernstein et al., 2001). Short interfering RNAs derived from Dicer activity are typically about 21-23 nucleotides in length and comprise about 19 base pair duplexes. When dsRNAs are transfected directly into mammalian cells, they activate the interferon system and provoke non-specific gene suppression and cytotoxic response. siRNAs have proven to be effective at specifically silencing gene expression without causing any interferon response.

The siRNA molecules of the present invention encompass mouse ILEI siRNAS, which are useful for research to analyse the function of ILEI, and human siRNAs, which may be used in therapy of humans, e.g. for cancer therapy.

Based on the RNA sequence of human or murine ILEI, ILEI siRNA molecules with the ability to knock down ILEI activity can be obtained by chemical synthesis or by hairpin siRNA expression vectors (as described by Yu et al., 2002) or they may be custom-designed, e.g. by means of the commercially available Dicer siRNA Generation Kit (Gene Therapy Systems), which allows generation of a large number of siRNAs from full-length target genes. The Dicer siRNA Generation Kit mimics the natural RNA interference process by using recombinant human dicer enzyme, to cleave in vitro transcribed dsRNA templates into a pool of 22 bp siRNAs.

There are numerous other companies that provide the supply of costume-designed siRNAs on a given RNA sequence, e.g. Ambion, Imgenex, Dharmacon.

The ILEI siRNAs of the invention may be chemically modified, e.g. as described in US 20030143732, by phosphorothioate internucleotide linkages, 2'-O-methyl ribonucleotides, 2'-deoxy-2'-fluoro ribonucleotides, "universal base" nucleotides, 5-C-methyl nucleotides, and inverted deoxyabasic residue incorporation.

In a further embodiment, the present invention relates to an expression vector comprising a nucleic acid sequence encoding at least one ILEI siRNA molecule in a manner that allows expression of the nucleic acid molecule, and cells containing such vector. Suitable expression vectors can be DNA plasmids or viral vectors, e.g. based on adeno-associated virus, retrovirus, adenovirus, or alphavirus, as described in US 20030143732.

The ILEI siRNA molecules of the invention may be delivered by known gene delivery methods, e.g. as described in US 20030143732, including the use of naked siRNA, cationic lipid formulations, liposome formulations including pH sensitive liposomes and immunoliposomes, and bioconjugates including siRNAs conjugated to fusogenic peptides. Delivery of siRNA expressing vectors can be systemic, such as by intravenous or intramuscular administration or by any other means that would allow for introduction into the desired target cell (see US 20030143732).

With regard to short interfering RNA molecules, their use as inhibitors of the function of ILEI, in particular as active ingredients in pharmaceutical compositions for human therapy, the criteria described above for anti-ILEI antibodies apply.

In a further aspect, the present invention also encompasses, as ILEI inhibitors, ILEI mutant proteins or ILEI (mutant) protein fragments or peptides (in the following: "ILEI inhibitory peptides") or synthetic peptidomimetics derived therefrom that act as ILEI antagonists, i.e. molecules that bind to but do not activate the ILEI receptor and subsequently inhibit binding of the native ligand ILEI. (For identifying the yet unknown ILEI receptor, the ILEI protein can be used, e.g. by using biotinylated ILEI for co-precipitation and isolation of the receptor from lysed epithelial cells (EpH4).)

ILEI inhibitory peptides can be identified according to known methods, e.g. by combining bioinformatics analysis that identifies conserved structural elements with a method referred to as "peptide walking" (Wang et al., 2002; Gili and Pick, 1995). Peptide walking is useful for the identification of domains in the primary sequence of proteins interacting with other proteins, e.g. with receptors. Based on the sequence of ILEI (SEQ ID NO:2 and SEQ ID NO:4), by means of this method, large number of overlapping ILEI peptides, spanning the entire amino acid sequence of the biologically active ILEI protein can be prepared, e.g. by the so-called multipin synthesis method (Valerio et al., 1991) with various lengths and extent of overlap, and either free or modified ends. Prior to this peptide approach, recombinant fragments of the ligand may be designed and expressed in order to narrow down the region of interest.

The ILEI peptides are then tested for their potential anti-ILEI effect, e.g. in competition assays using native ILEI (e.g. radioactively or fluorescence-labeled) and membrane fractions of tumor cells. Using such method, ILEI's binding site(s) to its putative receptor can be narrowed down. The identified peptides are then, optionally after modification by site-directed mutagenesis, tested for their anti-tumor effect as described above. Based on identified peptides, peptidomimetics can be custom-designed by commercially available services provided by The Peptide Laboratory, Jerini.

With regard to ILEI inhibitory peptides and peptidomimetics, their use as inhibitors of the function of ILEI, in particular as active ingredients in pharmaceutical compositions for human therapy, the criteria described above for anti-ILEI antibodies apply.

Depending on the indication, anti-ILEI antibodies (or antibody fragments or conjugates), antisense, ribozyme and siRNA molecules, inhibitory peptides and peptidomimetics may be combined with other agents, e.g. anti-cancer agents such as conventional chemotherapeutics like the drugs described above in the context with antibody conjugates, in particular taxanes, alkylating compounds, platinum compounds, topoisomerase inhibitors or antimetabolites, with hormones or anti-hormones or with antibodies like Herceptin and/or with radiotherapy.

In a further aspect, the invention relates to non-human ILEI transgenic non-human mammals. Such animals are useful for in vivo investigation of ILEI function.

In the meaning of the invention, ILEI transgenic non-human mammals are animals that carry as a transgene a DNA sequence encoding biologically active ILEI.

In a preferred embodiment, the transgenic animal is a mouse which carries a DNA sequence of SEQ ID NO:3 or a portion thereof.

Mice are usually used as transgenic animal models because they are easy to house and breed and relatively inexpensive. However, other non-human transgenic mammals may also be made in accordance with the present invention, such as but not limited to monkeys, sheep, rabbits and rats. ILEI transgenic animals carry the ILEI transgene; i.e. the cloned ILEI gene introduced, stably incorporated and passed on to successive generations. In the present invention, the mouse ILEI cDNA was cloned and stably incorporated into the genome of a mouse. Alternatively, altered portions of the ILEI gene sequence may be used. In this manner, the specific function of alternatively spliced gene products may be investigated during animal development and initiation of malignancy in order to develop therapeutic strategies.

The ILEI transgenic animals, e.g. mice, enable the analysis and elucidation of functional interactions of ILEI in a biologically relevant setting, and serve as a model for evaluating the efficacy of agents targeting ILEI. The transgenic mice of the present invention also allow for the development of various treatments for cancer, fibrosis, lung fibrosis or chronic obstructive pulmonary disease (COPD), chronic bronchitis; asthma including the identification and testing of various therapeutically active agents, including but not limited to antibodies, other proteins, peptides, peptidomimetic drugs, small molecule drugs, chemicals and nucleic acid based agents.

To investigate the in vivo function of ILEI, different lines of ILEI transgenic mice are generated. These mice can be used to identify the pathogenic effect of elevated ILEI level in mouse tissues. For this purpose, the Cre-Lox system can be used which allows the ubiquitous expression of ILEI or tissue-specific or inducible expression in different stages of mouse development or mouse lifetime. Histopathologic analysis reveals if overexpression ILEI is sufficient to induce aspects of the disease of interest (in particular cancer, fibrotic diseases or COPD) e.g. tissue remodeling or infiltration of immune cells.

If some of these mice develop symptoms that suggest the involvement of ILEI, these animals are used to investigate the therapeutic effect of ILEI inhibitors like anti-ILEI antibodies (or antibody fragments or conjugates), antisense, ribozyme and siRNA molecules, inhibitory peptides and peptidomimetics. The administration of ILEI inhibitors in this animal model may be combined with other therapeutic agents, e.g. conventional immunosuppressives like cyclooxygenase inhibitors (e.g. Ibuprofen, Indomehacin, Piroxicam), conventional chemotherapeutics like the drugs described above in the context with antibody conjugates, e.g. taxanes, alkylating compounds, platinum compounds, topoisomerase inhibitors or antimetabolites, with hormones or anti-hormones or with antibodies like Herceptin and/or with radiotherapy.

EXAMPLES

In the experiments of the invention, if not otherwise stated, the following materials and methods were used:

a) Cells and Cell Culture

The origin and culture conditions for EpH4 mouse mammary epithelial cells and their Has-Ras-transformed derivatives (V12-Ras-, S35-Ras-, and C40-Ras-expressing have been described earlier (Reichmann et al., 1992; Oft et al., 1996, Janda et al. 2002a). EpH4 cell derivatives were generated by retroviral gene transfer using infectious supernatant of the virus packaging cell line GPE (Mouse fibroblasts, ATCC) described in Journal of Virology, Markowitz et al., 1988).

Generating of GPE Cells for infection of epithelial cells (EpH4 and derivatives):

60-70% confluent GPE cells were transfected, using Fugene 6 (Roche) and the Retroviral Vector construct (pM-SCV-IRES-GFP, which was prepared according to the method described by Paulus et al., 1996). In this vector "Gateway Cassette A" was inserted by blunt end ligation. The ILEI cDNA was amplified from a EpRas ex-tumor cDNA (cDNA cloning kit Roche) using gateway compatible vectors, see below). The cDNA was inserted into this vector by homologous recombination (Invitrogen). Before infection, the medium of near confluent GPE cultures was changed and after 24 hours the supernatant, containing infectious retroviruses was harvested. Polybrene (Sigma) was added to a final concentration of 5 µg/ml and 6 ml sterile filtrated supernatant (0.45 µm filter) was added to the corresponding epithelial cells (60-70% confluence) in each 10 cm dish. Cells expressing the ILEI_IRES_GFP RNA were enriched by FACS-sort 5 days after transfection/infection. FACS sort was repeated 1-2 times for high level of GFP positive cells, typically over 70% GFP positive cells. Single infected epithelial cells were isolated by FACS selection.

Cultivation of Ex-tumor cells: Mouse tumors were recultivated from minced tumors after digestion with 10× trypsin (Gibco, BRL) for 30 min. Dispersed cells were seeded in Eagle's medium plus 15% FCS, selected for 14 d in 30 mg/ml ciprofloxacin (Roche) to prevent *mycoplasm* infection, and subcultured at a ratio of 1:3 every 2 d.

b) Induction of Tumors and Metastases in Mice

To test the various cell types for tumorigenicity, groups of three to eight Balb/C athymic nude mice (nu/nu; 5-9 wk old; obtained from Charles River Wiga, GmbH, Sulzfeld, Germany) were used for each cell type per experiment. Confluent cells, splitted the day before were trypsinized, washed three times in PBS and diluted to final concentration of $2 \times 10^6$ cells per ml. 20 µl was injected into the 3rd and 4th mammary gland pairs of anaesthetized mice (Avertin 2.5% (0.15 ml per 10 g body weight), shallow injection into the nipple area). Mean tumor diameter was calculated as the sum of diameters of all tumors after tumor isolation divided by the number of injection sites.

For the experimental metastasis assay, 50 000 cells suspended in 100 µl PBS were injected into the tail vein of nu/nu mice. Mortality due to lung metastasis was assessed daily. After the first mouse had died, all other mice were sacrificed, analysed for metastases in major organs and processed for histopathological analysis. For this, lungs were fixed in PFA 4% in 250 ml HEPES, pH 7.3 for 24 h, incubated with sucrose, 20% in 250 ml HEPES for 24 hours and embedded in Tissue-Tek (Secura, Netherlands). Sections were cut at 12-20 µm steps and stained with hematoxylin and eosin according to standard protocols.

c) Western Blot Analysis

Cells to be used for Western blot analysis of either serine-phosphorylated or total Erk and Ras proteins were 70% confluent and cultured in 4% FCS or starved for 48 h (for phospho-Akt and total Akt). Plates were washed with PBS and cells were lysed on ice with kinase buffer (10 mM Tris, pH 7.6, 50 mM NaCl, 1 mM EGTA, 1% Triton X-100, 50 mM NaF, 30 mM sodium pyrophosphate, 10 mM Na3VO4, and cocktail of protease inhibitors Complete™ both from Roche), centrifuged at 12,000 g for 10 min at 4° C. Either the supernatant or the pellet were loaded on gel. Freshly prepared lysates were analyzed by 8-12% SDS-PAGE and immunoblotted as described by Yu and Sato, 1999. ILEI expression was analyzed by 12% SDS-PAGE followed by Western blot analysis as above.

d) Collagen Gel Cultures

Serum-free three-dimensional cultures of EpH4 cells, EpRas cells, and their derivatives were carried as described earlier (Oft et al., 1996, 1998) Confocal analysis of collagen structures was performed using a Leica TCS-NT confocal microscope (DAPI visualized by two-photon excitation microscopy using Coherent-Vitesse pulsed NIR laser).

e) Immunofluorescence Staining of Cells Grown on Porous Supports

Cells were cultivated on porous supports (cell culture inserts, pore size 0.4 µm; Becton Dickinson) for 2-7 d and fixed either at 70% confluency (or as fully confluent well-polarized epithelial sheets). Filters were rinsed twice with Hanks solution plus glucose or PBS, fixed in acetone/methanol (1:1) for 5 min at −20° C., dried, washed with PBS, and blocked for 1 h in 0.2% gelatin in PBS-containing nonimmune goat or bovine IgGs (20 µg/ml) and 0.05% Tween. Filters were then incubated with first antibody (diluted in blocking solution lacking nonimmune IgGs) for 1 h, washed five times in PBS containing 0.05% Tween, treated with similarly prepared dilutions of secondary antibodies for 30 min, and washed again as above (first wash containing DAPI; 1 mg/ml stock, final dilution 1:10,000). Alexa-conjugated secondary antibodies against rabbit or mouse IgG (Molecular Probes, Inc.) were diluted 1:1,000, whereas Cy3-conjugated goat anti-rabbit or anti-mouse IgG (Jackson ImmunoResearch Laboratories) were diluted 1:300.

Tumor slides were stained identically to that protocol, starting with the blocking step. Staining of collagen gels was performed as described by Janda et al., 2000 a.

f) Detection of Secreted TGFβ

$3 \times 10^5$ cells were seeded on a 6 well plate (NUNC) and cultured for 24 hours. Medium was removed and cells were washed extensively with PBS (3 times) and serum free media (3 times). 1 ml of serum free media was added to the cells and supernatant was centrifuged after 16 h. Secreted TGFβ1 was detected, using a TGFβ1 Emax Immuno Assay System (Promega, Madison).

g) Cell Proliferation Assay

Cell proliferation was measured using the Cell Proliferation Kit I (MTT based, Roche). For this 500-1000 cells were seeded into each well of a 96 well plate. When the confluence of the highest proliferating cell clone was above 60%, all cells were trypsinized and splitted 1:10 before re-seeding.

h) Transmigration Assay

For each hole of a 12 well plate, 100 000 cells were seeded on a filter inlet (Greiner, 3 µm pore size) and cultivated for 36 hours. Supernatant was removed and transmigrated cells were selected by incubating the filter in a new 12 well plate filled with 0.75 ml 10× trypsin for 5 minutes at 37° C. The bottom of the filters was washed with 2 ml media containing 10% FCS. Transmigrated cells were counted under a light microscope.

i) Wound Closure Assay

Cells were seeded on 10 cm plastic dishes and cultivated until confluency. Medium was removed and cells were washed 5 times with PBS and cultured for 20 h in serum free media. After scratching (1.3 mm-2.9 mm) of the cell monolayer, cells were washed 5 times with PBS and cultivated in serum free media until wound closure. Wound closure was quantified by the average closed area of 15 microscopic areas (each representing 3 mm of the wound).

j) Production and Purification of C-Terminally Tagged ILEI

For mammalian expression, ILEI cDNA was generated as described with the exception that the stop codon was deleted from the primer sequence to obtain a C-terminal tagged fusion protein. The amplified ILEI c-DNA was inserted into the pCDNA-V5-His vector (Invitrogen) by recombination (GATEWAY).

ILEI was transiently expressed by COS7 cells (ATCC) after transfection with pcDNA-ILEI-V5-His vector (Invitrogen). Cells were therefore transfected with FUGENE 6 (Roche) according to the customer protocol. After 20 hours supernatant was changed and 24 h later cells were washed 3 times with PBS. After 48 h supernatant was harvested and either concentrated by Centriprep-10 (Amicon) or purified by Qiagen Ni-Chelat (Qiagen) using plastic columns (BioRad) according to the customers protocol. Buffers: Washing buffer 300 mM NaCl, 20 mM Imidazol, 50 mM NaH2PO4, elution buffer 300 mM NaCl, 300 mM Imidazole in 50 mM NaH2PO4 buffer. Eluated protein was dialyzed in 1× in PBS and 1× in DMEM media for 24 h each (Spectra Por Membrane MWCO 15000, Spectrumlabs). Protein quantity and quality was detected by Western blot analysis with a monoclonal mouse anti V5 Tag (Invitrogen) or polyclonal rabbit sera against ILEI peptide.

k) Stimulation of Epithelial Cells with Recombinant ILEI

Undiluted supernatant of EpH4 cells overexpressing ILEI or concentrated supernatant of ILEI overexpressing COS7 cells was diluted 1:3 and added to cells that were grown 15-30% confluent. Media was changed every 48 h. Relative amount of ILEI in the supernatant was detected by Western blot analysis. For investigation of the downstream signaling of ILEI, EpH4 cells were incubated with supernatant of EpH4 ILEI cells compared to EpH4 cells for 30, 60 and 120 minutes. Cell lysates were harvested and prepared for Western blot analysis and gel shift analysis as described elsewhere.

l) Reversion of Mesenchymal Phenotype:

Cells were seeded at 10-20% confluence and cultivated for 16 hours in 30% supernatant. After washing 3 times with media cells were cultivated in fresh media containing 10% FCS whereas control cells were cultured in media containing 30% supernatant of EpH4_ILEI cells.

m) Primers for Amplification of the Murine ILEI Open Reading Frame

```
SEQ ID NO: 5 (pcr_ILEI_s):
gggg aca agt ttg tac aaa aaa gca ggc tAA ATG AGGGT
AGCAGGAGCT SEQ ID NO: 6 (pcr_ILEI_as):
ggggaccactttgtacaagaaagctgggtGTCAGTCTTGCTT CTGGGGG
ATAC SEQ ID NO: 7 pcr_ILEI_as_for_C-fus:
ggggaccactttgtacaagaaagctgggtGGTCTTGCTTCTGGGGGATAC Amplified sequence (murine ILEI cDNA, SEQ ID NO: 3)
aaatgagggtagcaggagctgcaaagttggtagtggccgtggcagtattc ttactgaccttctatgttatttctcaagtatttgaaattaaaatggatgc aagtttaggaaatctatttgctcgatccgcgctggactcagccattcgtt ctacgaaacctccgaggtacaagtgtgggatctcaaaggcgtgcccagag aagcattttgcttttaagatggctagtggagcagccaatgtcgtgggacc
```

-continued

```
caagatctgcctggaggacaatgtttgatgagtggtgtgaagaataatg tcggaagaggaatcaatattgccttggtaaatgggaaaacaggggaagta atagacaccaaatttttgacatgtggggaggagatgtggcaccattcat tgagttttgaagaccatacaagacggaacagtagtgctaatggctacat acgatgatggagcaaccaaactcacggatgaggcacggcggctcattgct gaactgggcagcacttcgatcaccagtcttggtttccgagataactgggt cttctgtggtgggaagggcattaagacaaagagtcctttgaacagcaca taaagaacaataaggaaacgaacaagtacgagggatggcctgaggtggtg gagatggaaggatgtatccccagaagcaagactgac
``` n) Antibodies:

Mouse anti-E-cadherin (C20820; Transduction Laboratories); mouse anti-vimentin, Vim-13.4 (V-2258; Sigma-Aldrich)

Phospho-specific rabbit anti-phospho-Erk and anti-phospho-Akt antibodies and antibodies detecting total Erk1/2 and Akt were from New England Biolabs (9100 and 9270, respectively).

Rabbit polyclonal sera against murine ILEI Protein were generated by Gramsch Laboratories, Germany, according to the following protocol: 6 immunizations per rabbit (injection each 2-3 week) with 1.5 mg of the corresponding peptide (sequences described below), followed by 5 bleedings per rabbit with approximately 20 ml for each bleeding volume, starting 2 days after the second immunization and was repeated after further injections of peptide):

```
Peptide 1:                              (SEQ ID NO: 8)
mouse 96 C-VKNNVGRGINIALVNGKTGEVI 117

Peptide 2:                              (SEQ ID NO: 9)
mouse 189 C-GIKTKSPFEQHIKNNKETNKYEG 211
```

Comparison human/mouse sequence: 95% identity

```
                                        (SEQ ID NO: 9)
mouse: 189 GIKTKSPFEQHIKNNKETNKYEG 211

(SEQ ID NO: 10)
human: 189 GIKTKSPFEQHIKNNKDTNKYEG 211
``` o) Production and Purification of C-Terminally Tagged ILEI

For mammalian expression, ILEI cDNA was generated as described with the exception that the stop codon was deleted from the primer sequence to obtain C-terminal tagged fusion protein. The amplified ILEI c-DNA was inserted into the pCDNA-V5-His vector (Invitrogen) by recombination (GATEWAY).

ILEI was transiently expressed by COS7 cells (ATCC) after transfection with pCDNA-ILEI-V5-His vector (Invitrogen). Cells were therefore transfected with FUGENE 6 (Roche) according to the customer protocol. After 20 hours supernatant was changed and 24 h later cells were washed 3 times with PBS. After 48 h supernatant was harvested and either concentrated by Centriprep-10 (Amicon) or purified by Qiagen Ni-Chelat (Qiagen) using plastic columns (BioRad) according to the customers protocol. Buffers: Washing buffer 300 mM NaCl, 20 mM Imidazol, 50 mM NaH2PO4, elution buffer 300 mM NaCl, 300 mM Imidazole in 50 mM NaH2PO4 buffer. Eluated protein was dialyzed in 1× in PBS and 1× in DMEM media for 24 h each (Spectra Por Membrane MWCO 15000, Spectrumlabs). Protein quantity and quality was detected by Western blot analysis with a monoclonal mouse anti V5 Tag (Invitrogen) or polyclonal rabbit sera against ILEI peptide.

Production of recombinant (normal and His-tagged) ILEI and characterization of the binding specificity is summarized in FIG. 1c. Recombinant V5-His (t) tagged ILEI as well as non-tagged, native ILEI (n) secreted by transiently transfected Cos7 cells were detected in Western blots by anti V5 tag and anti ILEI antibodies. (c: Cos7 mock transfected supernatant; e: endogenous ILEI of EpH4 cells.) Anti V5 or ILEI-peptide specific antibodies were used for detection, e+o: ILEI antibody pretreated with oligo-peptide used for immunization.

p) Knock Down of ILEI Protein Level

To stably knock down the ILEI protein level in EpRas ex tumor cells two oligonucleotides

```
ILEIA_21_31A: TAA GAA TAC TGC CAC    (SEQ ID NO: 11)
              GGC CAC TAC CAA CGA
              AGC TTG GTT GGT AGT
              GGT CGT GGT AGT GTT
              CTT ATT GTT TTT T
and ILEI_21_31B:  TTA AAA AAA ACA ATA    (SEQ ID NO: 12)
              AGA ACA CTA CCA CGA
              CCA CTA CCA ACC AAG
              CTT CGT TGG TAG TGG
              CCG TGG CAG TAT TCT
              TACCGG
``` were synthesized and annealed by adding 10 µg of each oligo to boiling restriction-enzyme reaction buffer H (Roche Inc.). The mix was slowly cooled down to room temperature within 1 hour. The sequence of the oligonucleotides was selected according to the following protocol (Hairpin Protocol v2.1), which was developed for the design of shRNA inserts for pSHAG-1. Modifications of the protocol as used in this experiment concern the "Oligo ILEI_21_31B (SEQ ID NO: 12) as described below in 11) and 12). (available on the world-wide-web at cshl.org/public/SCIENCE/hannon.html.)

HAIRPIN PROTOCOL v2.1

Using sense, coding sequence of any gene.

(N1, N2, N30, N31, are numbered positions)

1) Find 5'-N1 NNNNN . . . NNNNNNNNNN C N30 N31-3'

The oligo must end in a "C" so that pol III, which initiates at a "G" in the U6 promoter, will initiate precisely at the first base of the antisense strand 2) Get reverse complement of (1) 5'-N31' N30'G N'N'N'N'N'N' . . . N'N'N'N'N'N'N'N'N1'-3'

3) remove N30' N31' to get 5'-G N'N'N'N'N'N'N' . . . N'N'N'N'N'N'N1'-3'

4) Add 5'-GMGCTTG-3' to 3'END to get 5'-G N'N'N'N'N'N'N' . . . N'N'N'N'N'N1'GMGCTTG-3'

5) OPTIONAL (to reduce hairpin formation by DNA oligos prior to ligation)

From (1) in positions N2 through N28 convert every third base possible from A to G or from C to T such that A) adjacent bases are not changed B) more than 4 bases are not changed C) homopolymeric runs greater than 6 bases in length do not result 6) To the 3'END of (4) ADD (5) to get 5'-G N'N'N'N'N'N'N'N' . . . N'N'N'N'N'N'N1'GMGCTTG N1 NNNNNNN . . . NNNNNNNN C N30 N31

7) Add pol III terminator TTTTTT to get 5'-G N'N'N'N'N'N'N'N' . . . N'N'N'N'N'N'N1'GMGCTTG N1 NNNNNNN . . . NNNNNNNN C N30 N31 TTTTTT 8) The inclusion of the HindIII site allows for rapid identification of clones containing a hairpin.

9) Drop G to get 5'-N'N'N'N'N'N'N'N' . . . N'N'N'N'N'N1'GMGCTTG N1 NNNNNNN . . . NNNNNNN C N30 N31 TTTTTT=oligo A 10) Get reverse complement of (9)

11) to (10) Add TTAA to 5' end 12) to (11) Add CCGG to 3' end=oligo B

Figure 7:
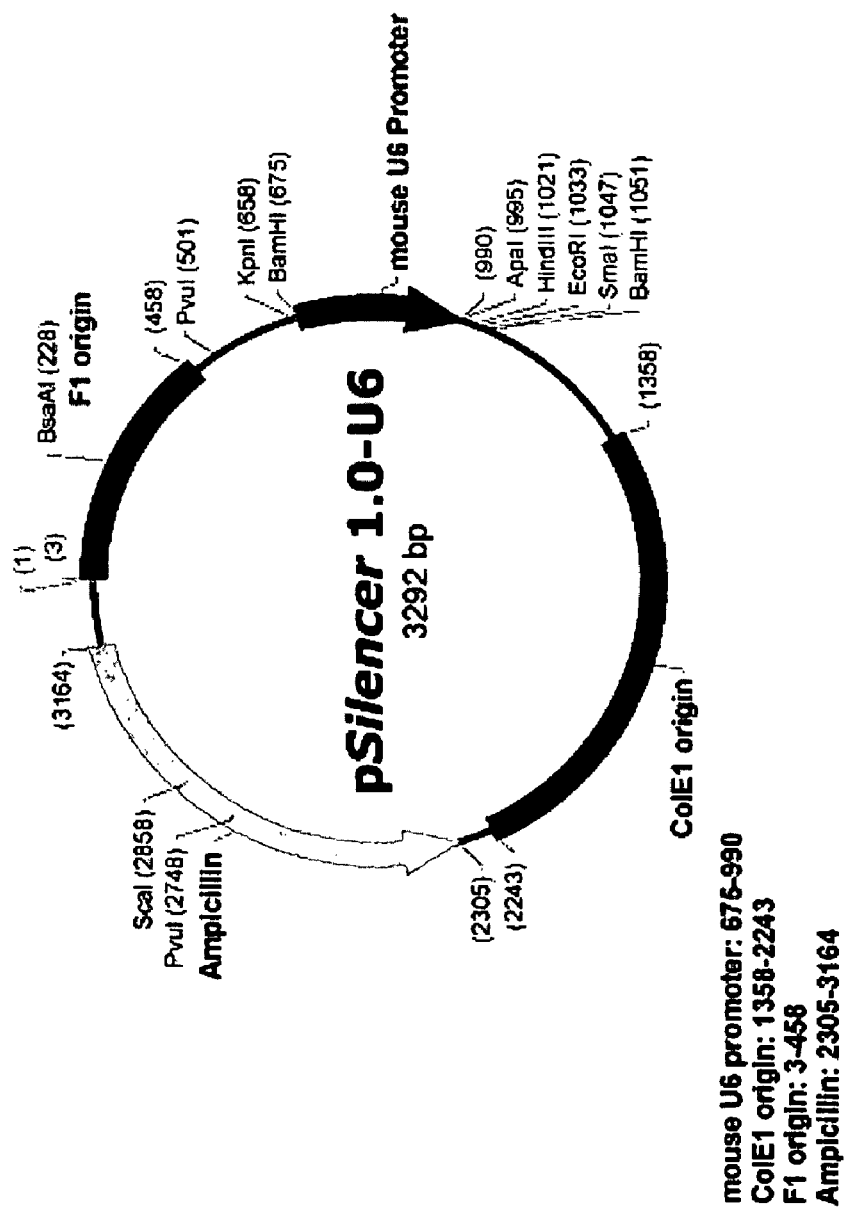
FIG. 7: Cartoon of the vector construct for expression of small interfering RNA molecules

Annealed oligos were ligated into ApaI/EcoRI cut pMSCV-GFP vector which was modified as described below for expression of small hairpin RNA (shRNA):

For generating a pMSCP-GFP vector suitable for shRNA expression, the following sequence was amplified from pSilencer 1.0-U6 siRNA Expression Vector (Cat. No. 7207Ambion, Inc.). For overview of the vector map see FIG. 7 (the sequence amplified for shRNA constructs contains BamHI site 575 to BamHI site 1051).

Amplified Sequence (gateway recombination sites are not included;

```
                                        (SEQ ID NO: 13)
Gatccgacgccgccatctctaggcccgcgccggccc
cctcgcacagacttgtgggagaagctcggctactcc
cctgccccggttaatttgcatataatatttcctagt
aactatagaggcttaatgtgcgataaaagacagata
atctgttctttttaatactagctacattttacatga
taggcttggatttctataagagatacaaatactaaa
ttattattttaaaaaacagcacaaaaggaaactcac
cctaactgtaaagtaattgtgtgttttgagactata
aatatcccttggagaaaagccttgtttgggcccccc
ctcgaggtcgacggtatcgataagcttgatatcgaa
ttcctgcagcccggggatcc.
```

This sequence was flanked by gateway compatible recombination sites using the following primers:

```
Primer 1 (forward):                     (SEQ ID NO: 14)
gggg aca agt ttg tac aaa aaa gca ggc
tga tcc gac gcc gcc atctct Primer 2 (reverse):                     (SEQ ID NO: 15)
ggggaccactttgtacaagaaagctgggtggatccc
ccgggctgca
```

Figure 3A:
FIG. 3: Expression of ILEI induces EMT
Figure 3A:
Figure 3A:
Figure 3A:

Using the gateway compatible recombination sites. The amplified sequence was inserted by recombination into the gateway compatible pMSCV-IRES between the T3 and T7 sites. The resulting construct contains the human U6 Promoter and a cloning site for insertion of the ILEI shRNA construct as described above (=shRNA cassette). The whole shRNA cassette is flanked by two recombination sites which allows sequence transfer into further "Gateway" compatible vectors (Invitrogen Inc.) using LR clonase enzyme. Using the gateway compatible vector pMSCV_GFP (described above) cells expressing the shRNA construct also expresses GFP protein by an independent promoter. GFP-positive cells were sorted by a FACS-Sorter (Fluorescence activated cell sorter, Beckton & Dickingson Inc.) and single cells were cultivated as described in (a). Intracellular expression of ILEI was assayed by Western blot analysis and functionality of the designed vector construct was assayed by Western blot indicating strong down regulation of ILEI protein which is also shown in FIG. 3c.

q) Treatment of Cells with Antibodies Raised Against ILEI

To investigate the effect of putative ILEI functional blocking antibodies on cells, mesenchymal EpH4_ILEI cells and epithelial EpH4 cells were seeded in 96 plates with a density of 1000 cells per well. Peptide 2 (mouse 189 C-giktk-spfeqhiknnketnkyeg 211; SEQ ID NO: 9) was used for affinity purification of rabbit peptide serum (for generation of peptide sera see "o") Purification of antibodies was performed with Gluthatione Sepharose 4B (prepacked disposal column according to the manufacturer's protocol (Amersham Inc. Cat. No 17-0757-01). The column was washed with 10 ml PBS. Purification of antibodies was performed at 4° C. 10 ml of rabbit sera was added to the affinity column and flowthrough was twice added to the column. The column was washed with 10 ml coupling buffer (0.1 M NaHCO$_3$, 0.5 M NaCl, pH 8.0 and 10 ml pre-elution-buffer (10 mM Na$_2$HPO$_4$/NaH$_2$PO$_4$ buffer, pH 6.8). Antibodies were eluated from the column with 0.1M Tris-Glycine pH. 2.7 in 1 ml aliquots and immediately neutralized using 2M Tris buffer, pH 8. The column was finally washed with 25 ml PBS and stored in 0.1% sodium acid/1×PBS at 4° C. Purified Antibodies (1 mg/ml) were added to the cells with a final concentration of 20 μg/ml (2 μl per 100 μl culture media Gibco DMEM with non essential amino acids, plus 5% fetal calf sera. As control for specific function of the antibodies, neutralized Elution buffer and antibody pre-incubated for 30 min with 4 mg/ml peptide 2 was added to the cells instead. The viability of cells was measured using Cell Proliferation Kit 1 (Roche Inc. Cat. No. 1465 007) according to the manufacturer's protocol.

r) Isolation of Total and Polysomal RNA and Quantitative RT-PCR

Primers used for quantitative detection of ILEI RNA:

```
Pcr ILEI s (SEQ ID NO: 16):
AAATGAGGGTAGCAGGAGCT

Pcr_ILEI_as (SEQ ID NO: 17)
AACATTGTCCTCCAGGCAG
```

ILEI polysomal RNA was isolated by sucrose gradient fractionation:

Sucrose Gradient Fractionation and RNA Analysis

Sucrose gradient fractionation and RNA analysis was performed as described (Mikulits et al., 2000). From each sucrose gradient, fractions 1-8 (containing free mRNPs and tRNAs) and fractions 11-20 (containing polysome-bound RNAs) were pooled. RNA was purified using the RNeasy kit (Qiagen), treated with DNaseI (Qiagen) and poly(A+) mRNA was isolated from these pools using the Roche polyA+ isolation kit.

Total RNA was isolated using supplier standard protocol for RNeasey Mini Kit Cat. No 74704 (Qiagen Inc.). One tube RT-PCR was performed as described by the supplier (Roche Inc. Cat. No. 1888382). Either 15 or 19 cycles were performed.

s) Immunohistochemistry

Immunohistochemistry was performed as described previously (Heider et al., 1993). In brief, frozen tissue sections (5 μm in thickness) were fixed in acetone and thereafter incubated with the primary antibody for 1 hour at room temperature. After washing in PBS, sections were incubated with the secondary, biotinylated anti-rabbit IgG antibody. After additional washing steps sections were incubated with a streptavidin-biotin-peroxidase complex (DAKO, Glostrup, Denmark). Colour development was performed in aminoethylcarbazole for 10 minutes, thereafter sections were counterstained with hematoxyline. After embedding in aequous mounting medium slides were evaluated under a light microscope.

Example 1

Levels of ILEI Polysome-Bound RNA and of Secreted Protein are Upregulated in TGFβ/Ras Induced EMT To give an overview of the tumor progression stages of the used cell lines the capacity of these cells to form tumors and/or metastases in nude mice is shown in FIG. 1a. In vivo metastases/tumor assays are described in Methods (b). To determine if ILEI expression level correlated with tumor progression stage, ILEI translated RNA and protein levels were detected during TGFβ induced EMT process and in the following well-characterized cell models representing different tumor progression stages: I) The spontaneously immortalized murine mammary epithelial cell line (EpH4) and clonally related derivatives expressing VRas or truncated VRas II. The highly metastatic colon cancer cell line CT26 and its weakly tumorigenic derivative, expressing the dominant negative TGFβRII, CKR 2 (Oft, 1998; Oft, 1996; Grunert, 2003) (FIG. 1a). As can be seen in FIG. 1b, the level of polysome-bound ILEI-RNA was detected as specifically upregulated in all EpH4-derived cell lines which can undergo EMT after stimulation with exogenous TGFβ, correlating with their induction of metastases in vivo. The isolation of polysome bound RNA is described in Methods (r). The procedure for transcription and labeling is described in the manufacturer's protocol. RNA clean up was performed using RNeasy Mini Kit (Qiagen Inc.). cDNA synthesis: 5 μg of RNA were used for 1$^{st}$ strand synthesis using SSII RT Kit, (Gibco Inc); cRNA synthesis was performed using cRNA Synthesis Kit (IVT Inc.). cRNA concentration and length distribution was measured in Agilent bioanalyzer according to manufacturer's protocol (Agilent Inc.). Further steps were performed as described in the standard Affymetrix labelling and hybridisation protocol (Affymetrix Inc.).

Figure 1D:
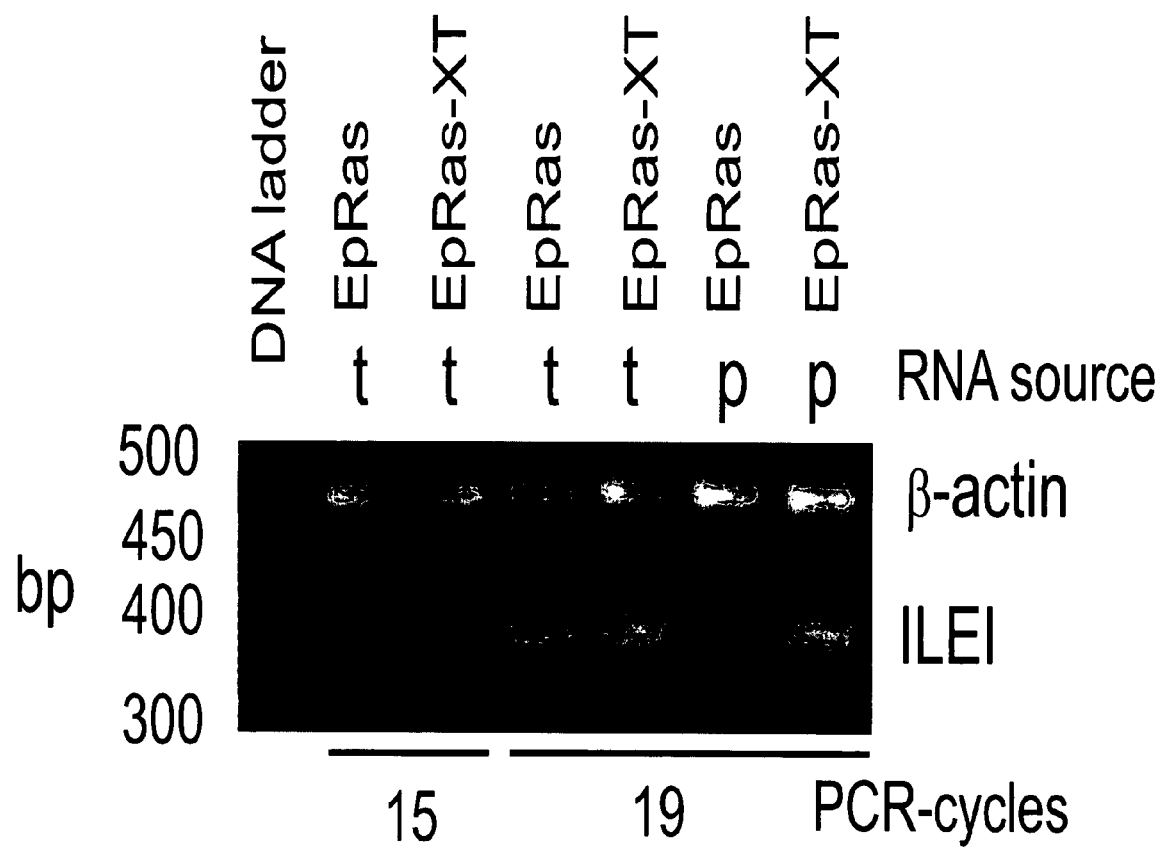

ILEI polysomal RNA was further upregulated in a second independent cell model, the highly metastatic colon cancer cell line CT26, as compared with its epithelial derivative CKR that expresses a dominant negative TGFβRII (FIG. 1b). The latter cells are weakly tumorigenic and not metastatic (Oft et al., 1998). Regulation of ILEI expression was detected using three independent assays: Affymetrix microarray Chip hybridisation, quantitative PCR (see Methods r), and Western (see Methods c) Blotting (FIG. 1b,d). The levels of polysome-bound ILEI RNA and secreted ILEI protein were specifically upregulated after induction of EMT. ILEI level was equal in TGFβ-induced scattering of apoptosis-protected EpH4_Bcl2 cells or Ep_C40 cells (FIG. 1b). Furthermore, oncogenic transformation with Ras or Bcl2 showed no effect on the ILEI level without TGFβ stimulation (FIG. 1b). Induction of ILEI during EMT is only controlled at the translational level. RT- PCR quantification of ILEI using total RNA (t) and polysomal bound RNA (p) (FIG. 1d).

Example 2

ILEI Protein can Induce EMT

To investigate if ILEI can promote EMT when stably expressed in epithelial cells EpH4, EpH4Ras, EpC40 and EpS35 cells were infected using a retroviral ILEI cDNA construct coupled with an IRES_GFP sequence. EpH4_ILEI, EpH4Ras_ILEI, EpC40Ras_ILEI displayed a fibroblastoid phenotype without additional exogenous stimulation (FIG. 3a). Translation of the polycistronic ILEI_GFP mRNA was proved by microscopical GFP detection and the secretion of enhanced levels of ILEI protein in infected cells was measured by Western blot analysis of media supernatant.

FIG. 3a shows epithelial cell morphology of EpH4 and flattened mesenchymal morphology in EpH4, EpRas and EpC40Ras cells expressing ILEI.

To further characterize the mesenchymal phenotype of EpH4_ILEI derivatives, the level of epithelial and mesenchymal marker proteins was investigated using Western blotting and immunostaining of cells cultivated on filters.

Figure 3B:
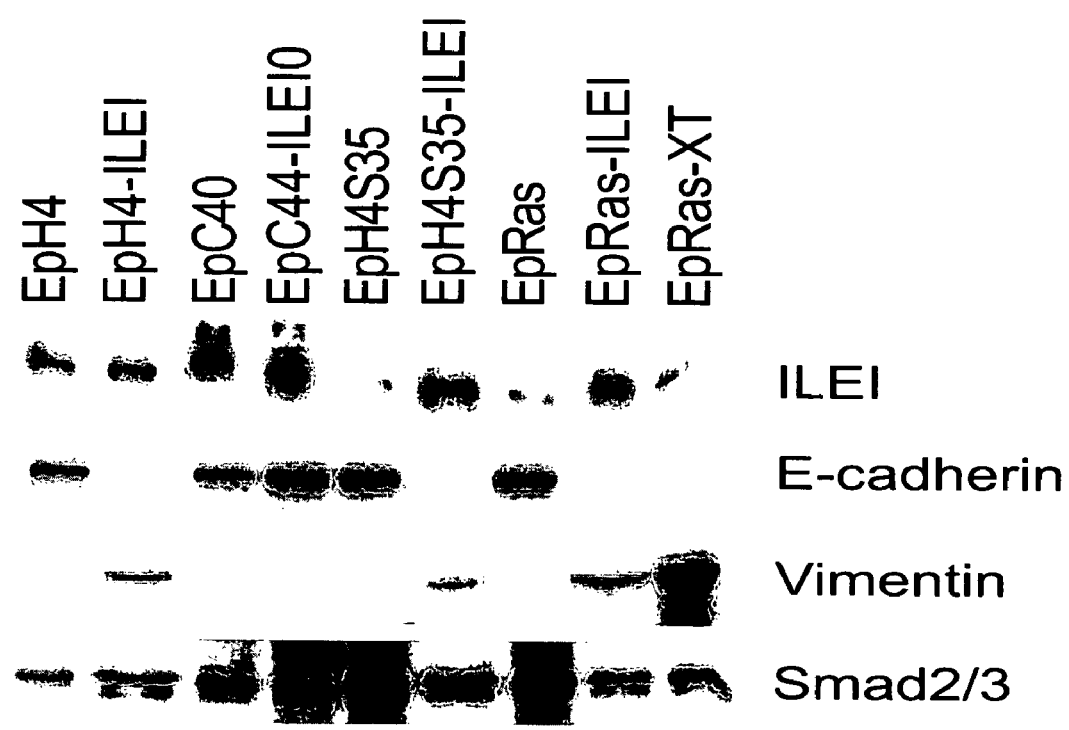
Figure 3C:

Results of a first experiment are shown in FIG. 3b: Stable ILEI expression induces EMT in EpH4, EpS35 and EpRas but not in EpC40 cells. Secreted ILEI from culture medium (top), E-cadherin (epithelial marker), and vimentin (mesenchymal marker, from cell extracts), were analysed in Western blots, and Smad 2/3 was used as a loading control (bottom). These results indicate that EpH4_ILEI, EpS35_ILEI, EpRas_ILEI have become negative for the epithelial marker E-cadherin which is a tight junction associated transmembrane protein. In these cells, E-cadherin protein was downregulated almost completely. On the other hand, these cells gained mesenchymal markers like the cytoskeleton-associated protein vimentin. EpC40_ILEI was one exception as it formed an epithelial layer when cells became confluent. Surprisingly, these cells overcame contact inhibition and formed areas with multiple layers on plastic plates. This was observed either for clonally mixed EpC40_ILEI cells or for each of 5 selected EpC40_ILEI single cell lineages. In cultures with high level of overgrowing EpC40_ILEI cells, E-cadherin was down-regulated marginally, but fragments of degraded E-cadherin were detected in Western blot analysis. FIG. 3 c shows down regulation of ILEI protein, when siRNA was stably expressed in EpRasXT cells after infection with an ILEI-siRNA retrovirus construct.

In another experiment, more sensitive analysis of 15 EpH4-GFP clones and 15 EpH4-ILEI clones that were derived from single cells revealed that E-cadherin is not completely absent, only its level is reduced. A significant fraction of E-cadherin was shown to be delocalized from the membrane to the cytoplasm, which is a hallmark of depolarized epithelial cells. Depolarization is necessary for detachment of epithelial cells out of an epithelial layer and results in higher motility. The mesenchymal marker vimentin is detectable in EpH4-ILEI cells, but not in EpH4-GFP cells as described earlier. As E-cadherin is still detectable in most clones of EpH4-ILEI, these cells might be in a transition phase of EMT. The partial EMT of most EpH4-ILEI clones can be explained by a lower ILEI level as compared to the clones used in the first experiment, as detected by Western blot analysis.

Figure 3D:
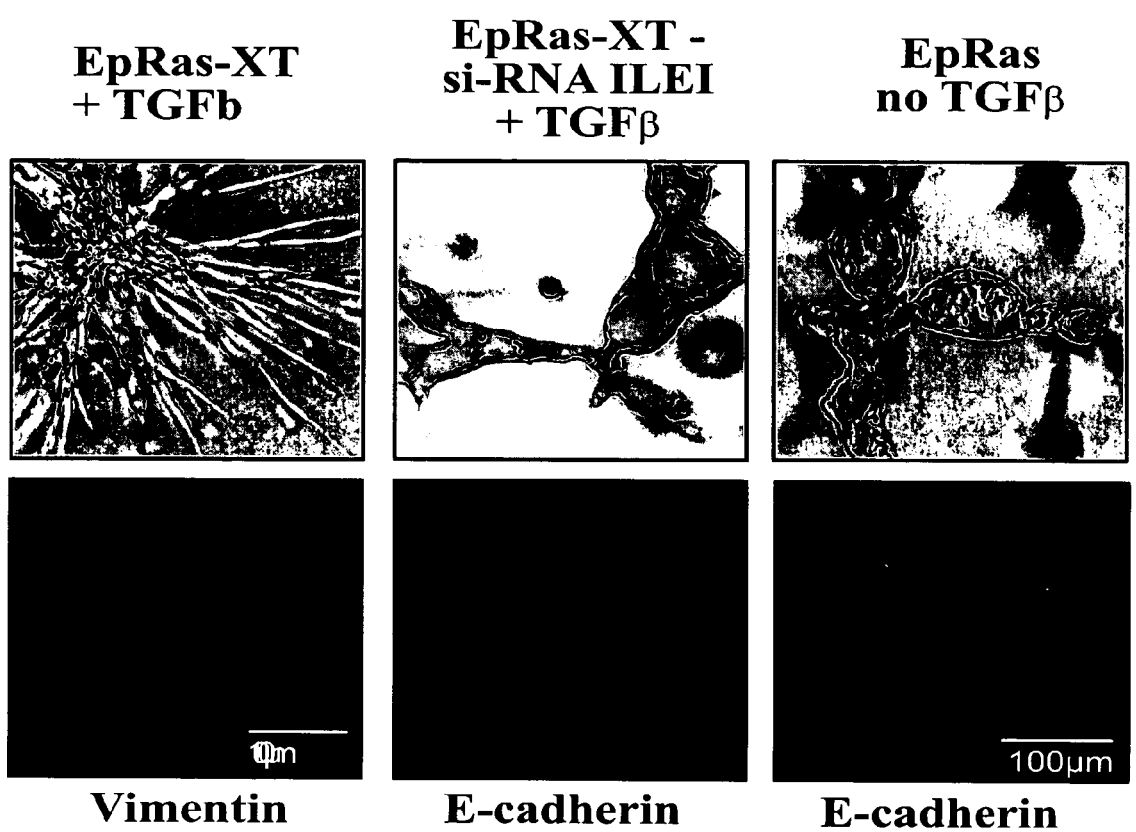
Figure 3E:
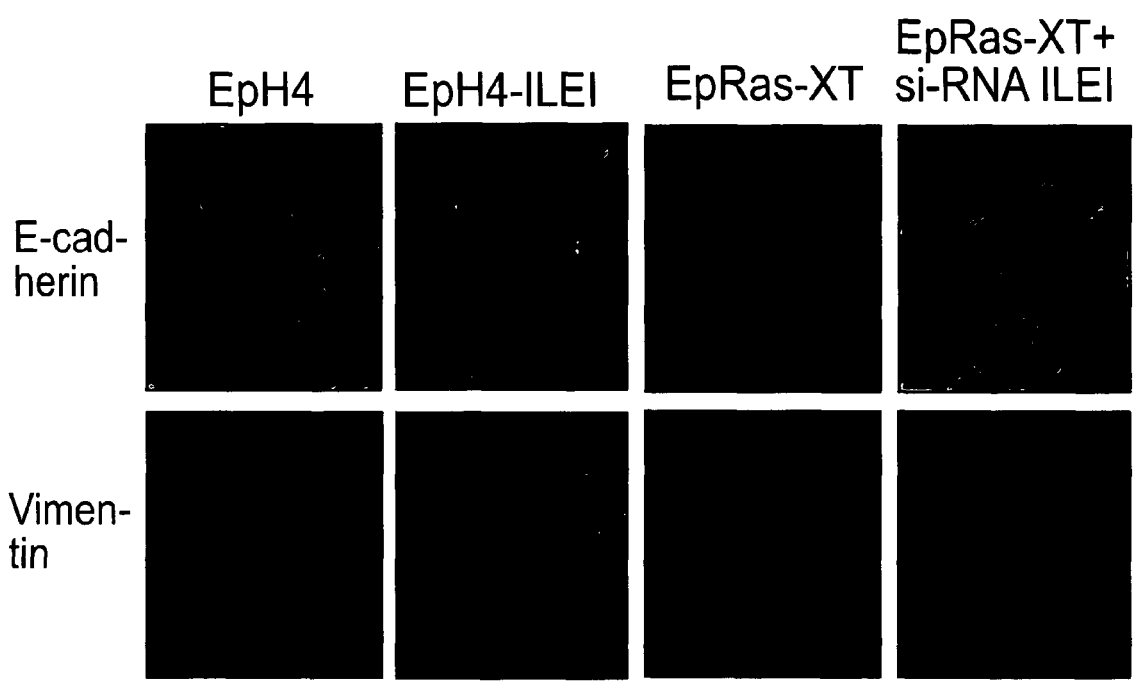

FIG. 3d indicates that knockdown of ILEI in metastatic EpRas-XT cells reverts EMT. Top panels: Collagen gel structures formed by EpRas-XT cells and the same expressing an ILEI-sh-RNA retrovirus (EpRasXT-ILEIsiRNA) in the presence of TGFβ. Control: EpRas cells minus TGFβ. Bottom: Structures formed by EpRas-XT cells stained with antibodies to vimentin, while the epithelial structures formed by EpRasXT-ILEIsiRNA and control EpRas cells stained positive for E cadherin. (3e) Immunostaining of E-cadherin or vimentin protein in EpH4 and EpH4_ILEI as well as EpRasXT and EpRasXT-siRNA-ILEI cells cultivated on filter correlated nicely with the data shown above, namely that ILEI induces EMT in EpH4 cells by upregulation of vimentin and knockdown of ILEI reverts the mesenchymal phenotype of EpRas ex tumor cells, indicated by upregulation of E-cadherin. Nuclei are visualized by DAPI stain.

Example 3

Expression and Analysis of Biologically Active Murine ILEI a) Expression

In one set of experiments, full-length murine ILEI cDNA (SEQ ID NO: 3, starting with ATG and terminating with TGA) was cloned into pcDNA 3.1 vector (Invitrogen) and expressed in FreeStyle™ 293-F cells (Invitrogen) by transfection with 293fectin (Invitrogen) according to the supplier's instructions.

In another set of experiments, murine ILEI cDNA (SEQ ID NO: 3, starting with ATG and terminating with TGA) plus a sequence encoding a C-terminal TEV cleavage site and a purification tag, was cloned into pcDNA 3.1 vector (Invitrogen) and expressed in FreeStyle™ 293-F cells (Invitrogen) by transfection with 293fectin (Invitrogen) according to the supplier's instructions. (The protein contained a C-terminal purification tag (SerHis$_6$) after the tobacco Etch Virus (TEV) cleavage site Glu-Asn-Leu-Tyr-Phe-Gln-Gly.)

Cell culture supernatants were collected after 72 hours and secreted ILEI purified by chromatography on Ni-NTA-Superflow (Qiagen). The His-tag was removed by incubation with TEV protease (Invitrogen) and muILEI further purified by gel filtration chromatography (HiLoad Superdex S200, Amersham Biosciences).

b) Analysis

The N-terminus of purified recombinant muILEI (as obtained by both sets of experiments) was analysed by Edman sequencing (494cLC Procise, Applied Biosystems) and subjected to mass spectrometry (Q-TOF Ultima, Micromass) after purification over a reversed phase C18 column.

In all except one batches, the N-terminal amino acid of secreted muILEI was identified as serine in position 42 (numbered according to SEQ ID NO:4, corresponding to Swissprot entry Q91VU0).

From one batch, the N-terminus was found to be heterogeneous. About one third of the material started at amino acid 42 (Ser), about one third at amino acid 41 (Arg) and about one third at amino acid 44 (Leu).

Recombinant material from all batches was found to be biologically active in functional assays (see Example 4).

Comparing the yield of each PTH-amino acid resulting from Edman sequencing, a substantial decrease was observed at Thr 51. This is most likely due to a post-translational modification. Mass analysis of the intact protein showed isoforms with higher masses compared to the theroretical mass derived from the DNA sequence. The determined masses of the additional components indicate the presence of an oligosaccharide composed of N-actyineuraminic acid, N-acetylhexosamine, and hexose modules.

Example 4

Figure 4A:
FIG. 4: Recombinant ILEI induces an invasive phenotype
Figure 4A:
Figure 4B:
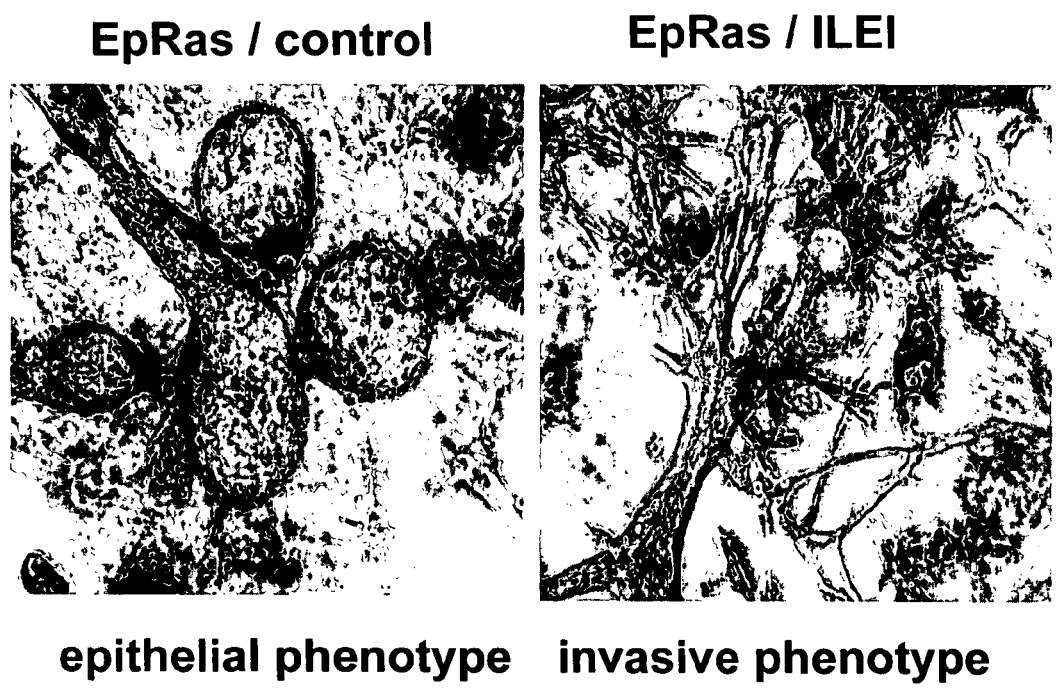

ILEI can Signal Via Autocrine and Paracrine Mechanisms a) To address the question whether ILEI signals extracellularly through a unknown receptor, EpH4 cells were cultivated with purified, recombinant ILEI protein (obtained by transient expression as described in Materials and methods, j) or were co-cultivated with EpH4_ILEI cells. Both sets of experiments showed a morphologic conversion from an epithelial to a mesenchymal/fibroblastoid phenotype which was dependent on the level of soluble ILEI protein in the corresponding supernatant. When EpH4 cells were cultured with supernatant of EpH4_ILEI cells for approximately 2 weeks, their colony morphology shifted from dense structures (epithelial) to sparse colonies with flattened cells of fibroblastoid shape (mesenchymal) This phenotype was induced earlier, namely after 4-6 days by culturing. EpH4 cells in supernatant of Cos7 cells that secrete recombinant ILEI protein. Supernatant of mock-transfected Cos7 cells did not induce a change in cell morphology or colony phenotype. Quantification of the ILEI protein level by Western blot analysis revealed a dose dependent decrease in time for this epithelial to fibroblastoid switch. By co-cultivation of EpH4 and EpH4_ILEI_IRES_GFP cells the EpH4 cell fraction undergoes EMT, indicated by de-localization of E-cadherin from the cell membrane at the same time when the colony formation becomes sparse. E-cadherin was completely absent after a 3 week co-cultivation containing 50% EpH4_ILEI cells (E-cadherin negative) and 50% EpH4 cells (E-cadherin positive). All cells in this culture gained a fibroblastoid shape and the mesenchymal marker vimentin which was detected in EpH4 cells indicates also an EMT process induced by EpH4_ILEI cells. Furthermore, strong dilution of the secreted ILEI protein level by daily media exchange of sparsely seeded EpRas_ILEI cells restored the epithelial phenotype of polarized cells to a large extent within 2 days. This correlated with elevated level of E-cadherin protein and redistribution of E-cadherin to the cell membrane.

b) Stimulation of EpH4 or EpRas cells (2500 cells per 100 µL collagen gel) with 1.6 µg/ml recombinant, purified ILEI as obtained in Example 3 at every second day revealed a strong change in the morphology of multi-cell organotypic structures after 5 days. Examples of organotypic cell structures and their invasive phenotype after ILEI stimulation are shown in FIG. 4a (EpH4) and FIG. 4b (EpRas). Epithelial cell structures are characterized by round cell aggregates and partial hollow structures (see FIG. 4 a,b,c left panels). After ILEI treatment cells detach from the epithelial structures and invade the collagen matrix. Invading cells are characterized by spindle like cell shape and result in elongated multi-cell structures (see FIG. 4 a,b,c right panels).

Figure 4C:
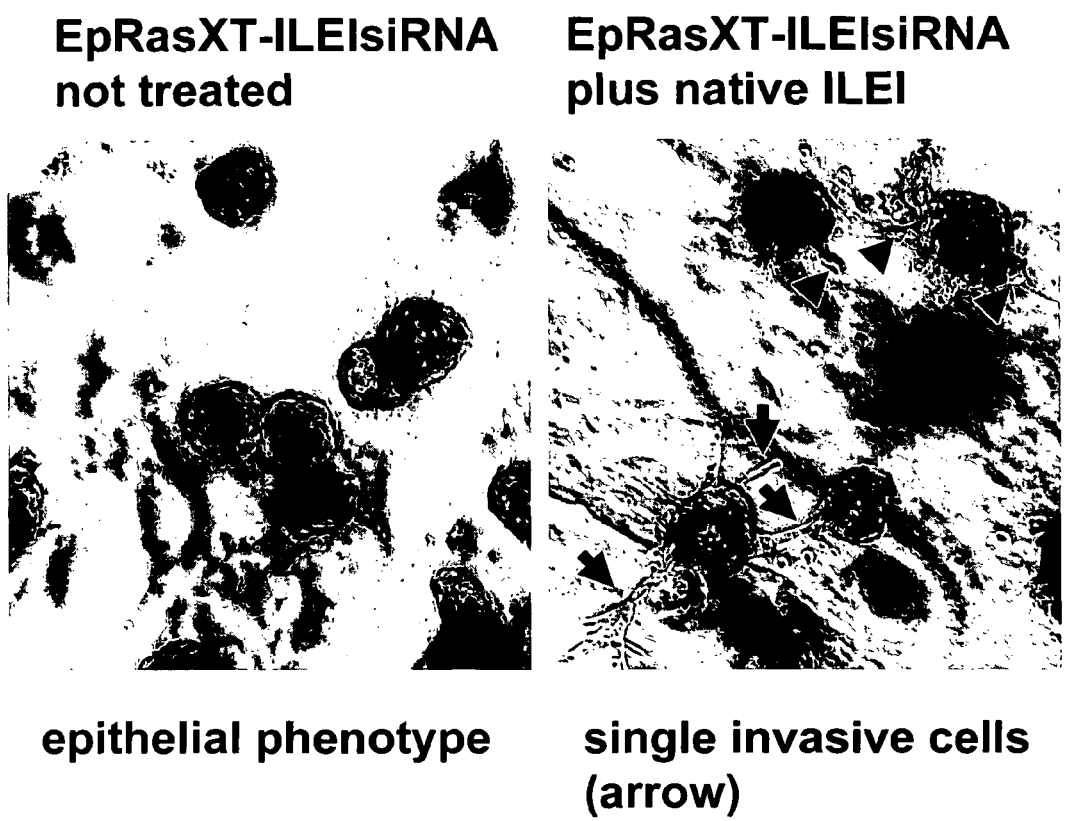

Stimulation of EpRasXT-ILEIsiRNA (these cells express almost no ILEI and are described in Example 2) with a second, recombinant ILEI product (purified recombinant ILEI, see Example 3) enhances the outgrowth of cells from epithelial clusters after 8 days of ILEI stimulation (final ILEI conc. 4 µg/ml). ILEI was added at day 2, 4, 6. Representative collagen structures of non treated EpRasXT-ILEIsiRNA are shown in FIG. 4c, left panel and cells that evade these structures after addition of recombinant ILEI are marked with arrows in FIG. 4c, right panel.

c) Single time stimulation of 500 EpH4 or EpRas cells with 1.6 µg/ml recombinant, purified ILEI (obtained in Example 3) 2 h after seeding into a 35 mm plastic dish (Greiner Inc.) results in an increase in cell motility. This ILEI effect can be used for further functional characterization of recombinant ILEI and for characterization of ILEI-functional blocking antibodies which might block the motility effect of ILEI, when pre-incubated with the recombinant ILEI protein. The cell motility effect could be investigated either by time-laps photography or by cell-based assay for motility of endothelial cells (e.g. Cellomics Inc.).

Example 5

ILEI Induces Marginal TGFβ Secretion

Figure 3F:
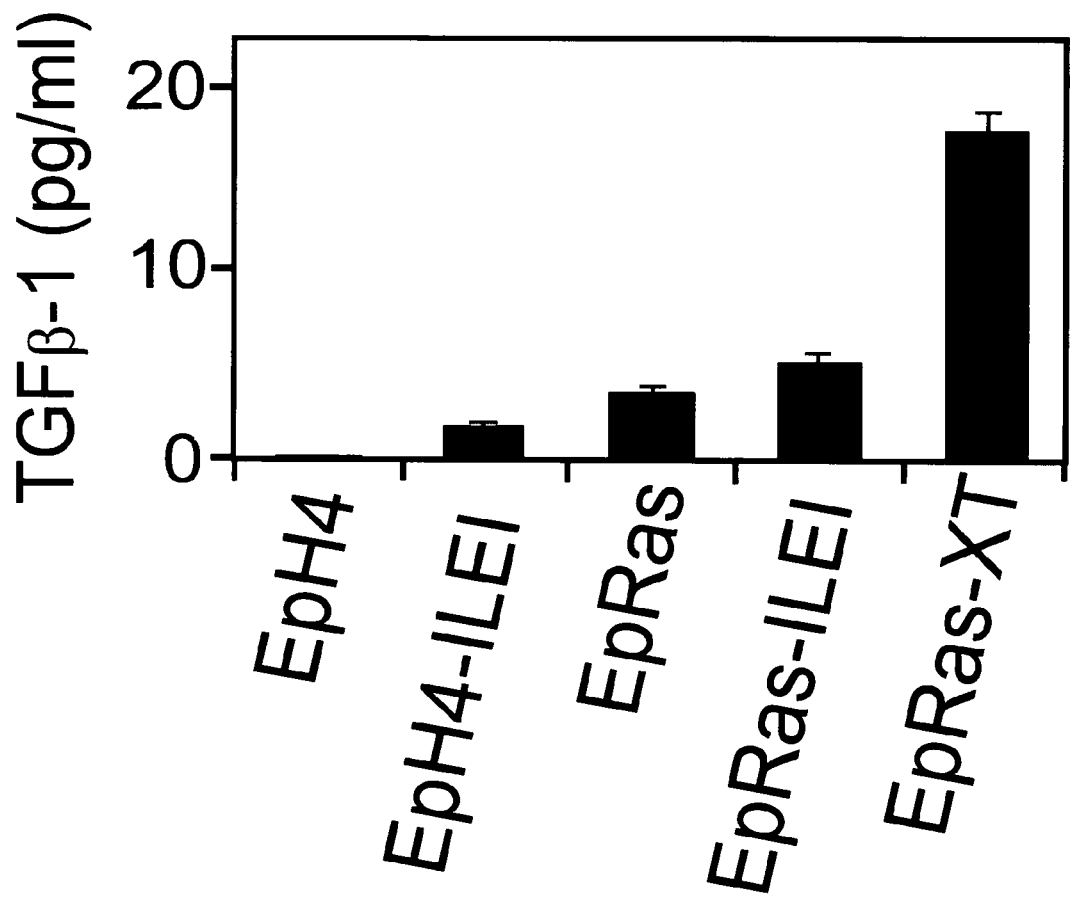

Earlier results in the inventors' laboratory have shown an autocrine TGFβ and PDGF loop in mesenchymal EpRas cells after TGFβ induced EMT, which correlated with an enhanced ILEI protein level. To investigate if mesenchymal EpH4_ILEI derivatives induce an equal autocrine TGFβ loop a TGFβ ELISA was performed to quantify the level of secreted TGFβ in the supernatant of the respective cell pairs. In none of the EpH4 derivatives, stable overexpression of ILEI induced a significantly enhanced level of secreted TGFβ comparable to the EpRas ex tumor cells. For EpH4_ILEI, EpC40_ILEI, EpS35 and EpRas_ILEI a marginally enhanced level of secreted TGFβ was measured, compared to their respective control, without ILEI overexpression. Compared to the EpRas ex tumor cells, which are characterized by a TGFβ autocrine loop, the level of secreted TGFβ was approximately 20 fold lower for EpH4_ILEI and approximately 4 fold lower for EpRAS_ILEI and EpC40_ILEI. ELISA quantification of TGFβ1 secreted by EpH4 and derivatives is shown in FIG. 3f.

Example 6

TGFβ can Rescue Growth Inhibition in EpH4_ILEI Cells that Occurs During ILEI Withdrawal As TGFβ is present in the blood stream and the tumor region, the influence of TGFβ on the proliferation and apoptosis rate of EpH4 and EpH4_ILEI was investigated. Therefore 500 cells of EpH4 and EpH4_ILEI, respectively, were seeded into each well of a 96 well plate (Greiner Inc.). 4-10 days after cell cultivation either with culture media (see Methods a) or media supplemented with 0.2-10 ng TGFβ treatment. At the endpoint of the investigation, cell proliferation was quantified using MTT proliferation assay (Roche Inc.) and apoptosis was calculated by counting DNA-DAPI stained nuclear fragments (Dapi 1:10000, Roche Inc.) which is a marker for late stages of apoptosis. TGFβ levels above 0.4 ng/ml inhibited cell proliferation and induced apoptosis in EpH4 and EpH4_ILEI indicating that ILEI expression does not induce a strong apoptosis protection as it is induced in EpHRas cells. EpRas cells were protected from TGFβ induced apoptosis even at levels up to 5-10 ng/ml TGFβ.

EpH4 cells proliferated well in DMEM media supplemented with 10% FCS and their proliferation rate was not significantly enhanced with addition of 0.2 ng/ml TGFβ. In contrast, proliferation of EpH4-ILEI cells without TGFβ was low and could be increased 2 fold when media was supplemented with 0.2 ng/ml TGFβ. The block of EpH4_ILEI proliferation was also overcome by adding 30% of EpH4_ILEI conditioned media containing secreted ILEI protein. This result indicated that stimulation by low concentrations of TGFβ or ILEI protein are sufficient for proper proliferation of EpH4_ILEI cells, which is then comparable to the proliferation of EpH4 cells. The importance of a low TGFβ protein level for proliferation of EpH4_ILEI cell derivatives was also detected in three dimensional collagen gel assays which mimics the tumor "in vivo" situation by collagen structures and allows serum free cultivation. Compared to typical epithelial hollow structures which were formed by EpRas cells (FIG. 3d), all EpH4_ILEI derivates seeded in collagen gels showed a dramatic decrease in cell proliferation. 48 h after seeding the EpH4_ILEI derivatives in the gel matrix formed extreme spindle shaped cell structures. A very low proliferation rate was detected by counting the cells and enhanced cell death was determined by GFP positive cell fragments (data not shown). Adding 1-5 ng/ml TGFβ either 24 h or 48 h after seeding EpRAS_ILEI cells into the collagen fully recovered normal cell proliferation and viability, resulting in the formation of E-cadherin negative and vimentin positive mesenchymal structures (data not shown).

Example 7

ILEI Activates STAT3 Alpha and Induces Cell Mobility

Figure 2B:
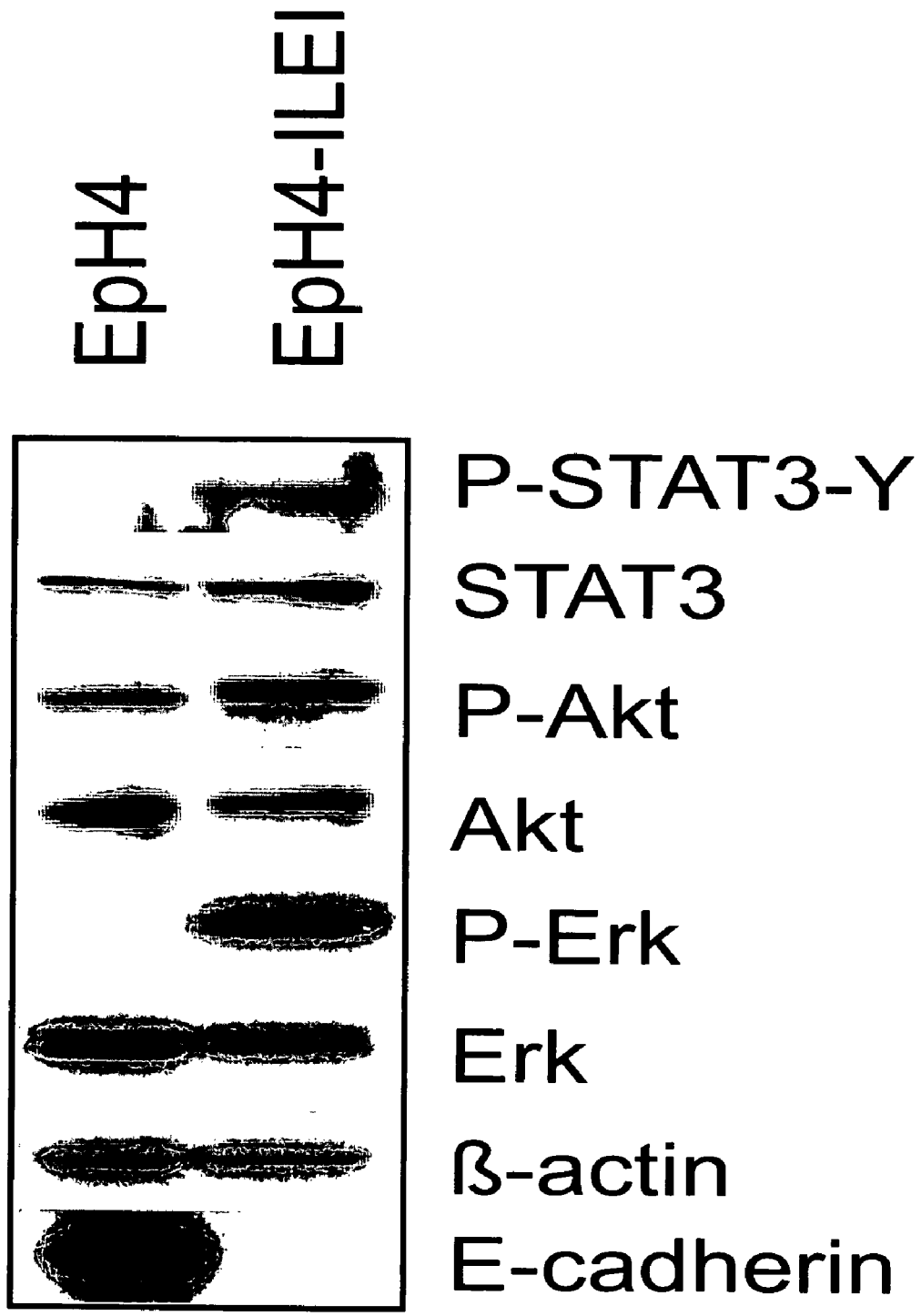
FIG. 2: STAT3α, P-Erk and P-Akt activation is induced by stable expression of ILEI or supernatant from ILEI expressing cells

The structural homology of ILEI to other cytokines encouraged the inventors to investigate whether ILEI signals via the Jak/STAT pathway, which is a commonly activated signaling route of cytokines. Strikingly, STAT3 was active in EpH4_ILEI cells, as shown in FIG. 2 a,b. Furthermore, a strong upregulation of active STAT3 level was detected within 30 min. after stimulation of EpH4 cells with supernatant of EpH4_ILEI but not with supernatant of EpH4. Active STAT3 level was detected by gel mobility shift assay and verified by antibody supershift assay (FIG. 2). (The methods used in this assay have been described by Moriggl et al., 1998). FIG. 2a shows EpH4-ILEI cells and EpH4 cells stimulated with EpH4-cell-ILEI supernatant or IL6 show enhanced levels of active STAT3α as detected by Gel Mobility Shift Assay. FIG. 2b shows Western blot detection of phosphorylated STAT3, Akt, Erk in EpH4-ILEI cells and downregulation of E-cadherin. β-actin was used for equal loading control.

Preliminary gene expression data obtained from RNA comparison of EpRas and EpRas-ILEI cells revealed increased RNA levels of proteins that can induce STAT3 phosphorylation in EpRas-ILEI cells (e.g. prostaglandinE synthetase, prostaglandinE receptor). (Expression profiling, hybridization and screening were done as described in Example 1.) These data suggest that STAT3 may be activated by ILEI not in a direct, but in an indirect way Given the involvement of ILEI in STAT3 activation and the known property of STAT3 cell motility, which is a feature of metastatic cells, the inventors investigated if ILEI expression can promote cell migration on plastic layer and if transmigration through porous filters can occur. In a wound closure assay confluently grown cells were serum-starved and the time was measured for closing an artificial scratch in the cell monolayer. The time for complete closure of the scratch was significantly reduced for EpC40_ILEI cells compared to EpC40 cells (EpC40 was 5 days until closure, which is a 2 days longer period). In the transmigration assay the number of EpC40_ILEI cells that transmigrated through the filter pores was 2.5 fold increased compared to EpC40 cells. These results indicated the pro-migratory effect of the ILEI protein.

Example 8

ILEI Enhances Tumorigenicity

Figure 5A:
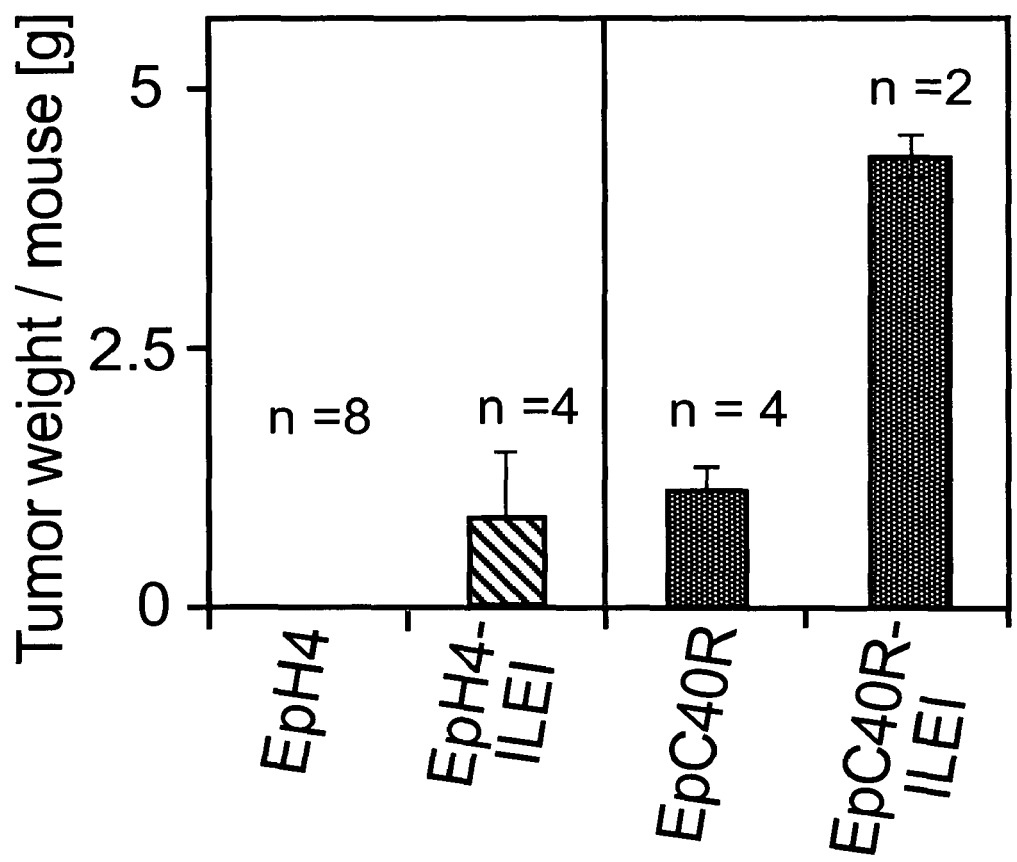
FIG. 5: ILEI induces or enhances tumor growth
Figure 5B:
Figure 5B:
Figure 5C:
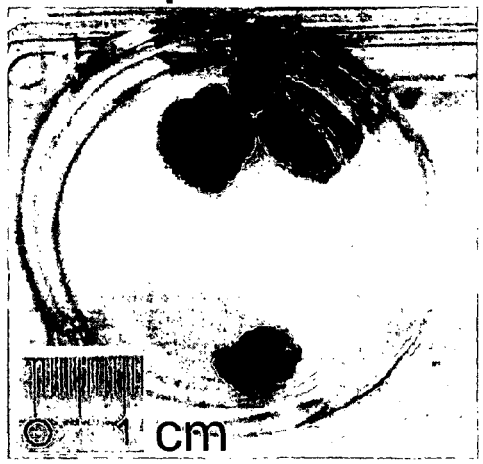
Figure 5C:
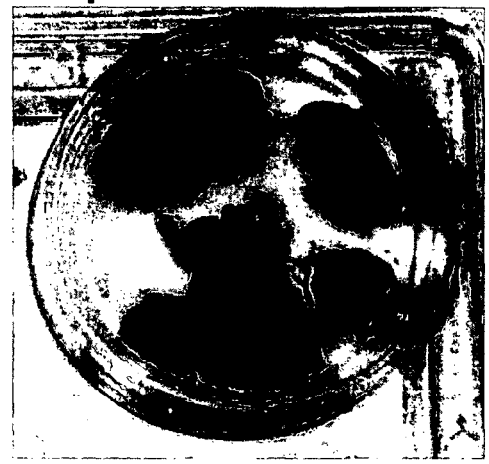

To determine the tumor promoting function of ILEI in vivo, EpH4 cells and their derivatives EpH4_ILEI, Ep_C40 (mutated RasC40, mainly PI3K signaling) and EpC40_ILEI were injected into four mammary gland fat pads of each nude mouse (see Methods b). Whereas EpH4 cells were unable to form tumors in any of the 5 injected mice, EpH4_ILEI cells formed tumors in 3 of 4 injected mice with a average tumor weight of 1.1 g/mouse after 16 weeks indicating that ILEI expression induces tumorigenicity in EpH4 cells. Furthermore, 8 weeks after injection of EpC40_ILEI cells the derived tumors weighed 4.3 g/mouse, which was a 3.6 fold increase in tumor mass compared to the EpC40, 1.2 g/mouse (FIG. 5). After dissection of the tumor and quantification of tumor size and weight, a small portion of the tumor cells was cultivated. Their origin from the injected cells was identified by GFP detection under a microscope. Histological investigation of thin layers of resected tumor tissue derived from EpC40_ILEI and EpH4_ILEI cells revealed a striking morphologic difference compared to EpC40 and EpRas cell derived tumors. About 70-90% of the cells within all tumors that developed from ILEI and GFP overexpressing cells showed a mesenchymal phenotype and were vimentin positive but E-cadherin negative. These cells formed porous, hollow structures in the tumor as shown in FIG. 5c. Within the tumor a second fraction of cells was detected, namely GFP negative cells that were E-cadherin positive but vimentin negative and formed dense epithelial structures, typical for EpC40 or EpRas derived tumors. It was not investigated if this fraction of epithelial cells was derived from the host organism and have infiltrated the tumor or if these cells are of EpC40_ILEI cell origin that somehow silenced ILEI and GFP protein expression. In contrast, tumors that arose from EpC40 showed mainly epithelial morphology with mesenchymal features only at the growth and invasion front of the tumor. FIG. 5 shows that ILEI induces or enhances tumor growth and causes tumor cells to undergo EMT (a) EpH4 and EpH4-ILEI cells as well as EpC40V12Ras (EpC40R) and EpC40R-ILEI cells were injected into the mammary gland area of nude mice ($0.5 \times 10^5$ cells per injection site, 4 injection sites per mouse) and the combined weight of tumors from all injection sites of one mouse was determined after 8 weeks or 14 weeks for EpH4 and EpH4ILEI. FIG. 5b: Large tumors induced by EpH4-ILEI cells 14 weeks after injection, as compared to small regressing nodules induced by parental EpH4 cells (which contain necrotizing epithelial cells (Oft et al., 1996). FIG. 5c: Tumors induced by EpC40R-ILEI cells showed larger size, a more "spongy" appearance and stronger vascularization than EpC40 tumors. EpH4-ILEI induced tumor cells showed absence of E-cadherin and presence of vimentin, indicating EMT in vivo. EpC40R-ILEI tumor cells showed a mesenchymal, dedifferentiated phenotype and no expression of E-cadherin in most areas of the tumors, while EpC40R induced tumors are more differentiated and express (delocalized) E-cadherin (Janda et al., 2002a). Regions of EpC40R-ILEI tumors positive for E-cadherin were shown to have lost GFP expression.

Example 9

ILEI Enhances Metastasis

Figure 6A:
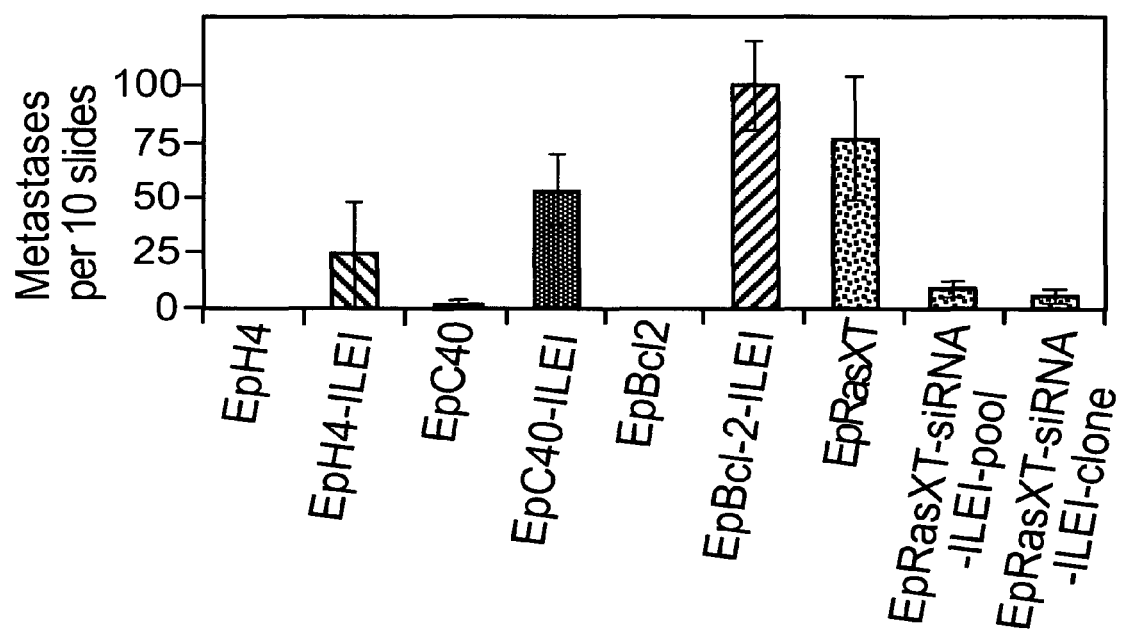
FIG. 6: ILEI induces metastasis formation, while knockdown of ILEI in metastatic tumor cells prevents metastasis
Figure 6B:
Figure 6B:
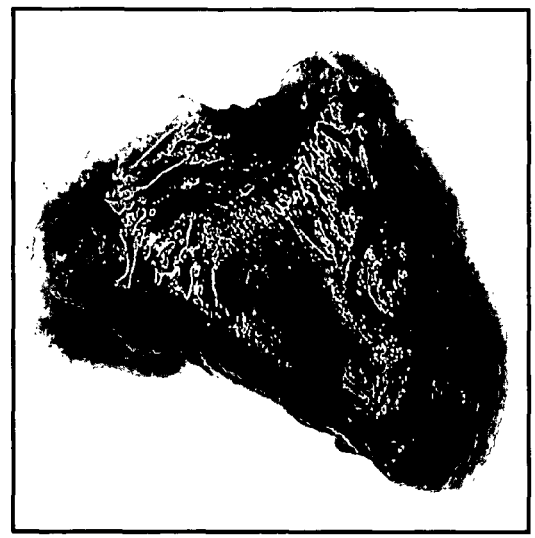
Figure 6C:
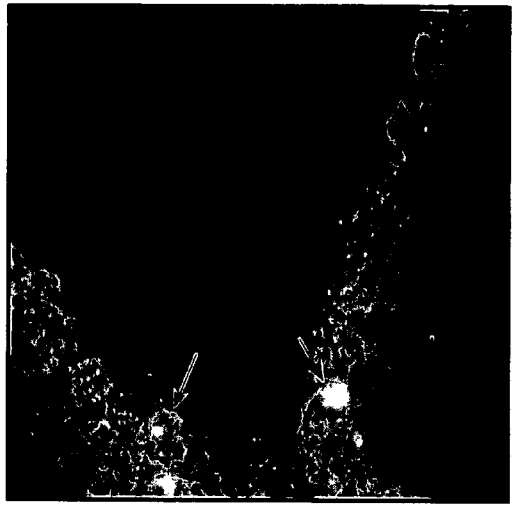
Figure 6C:
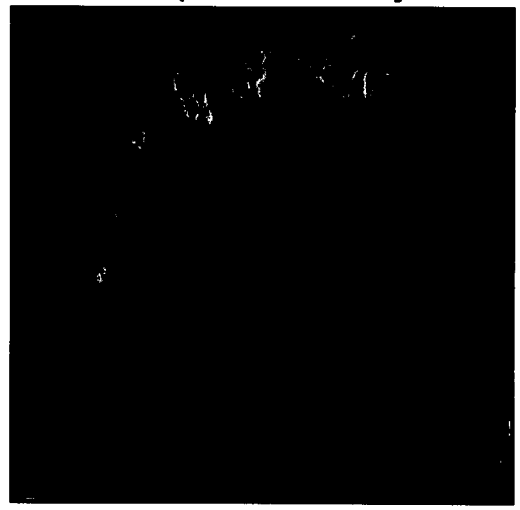
Figure 6D:
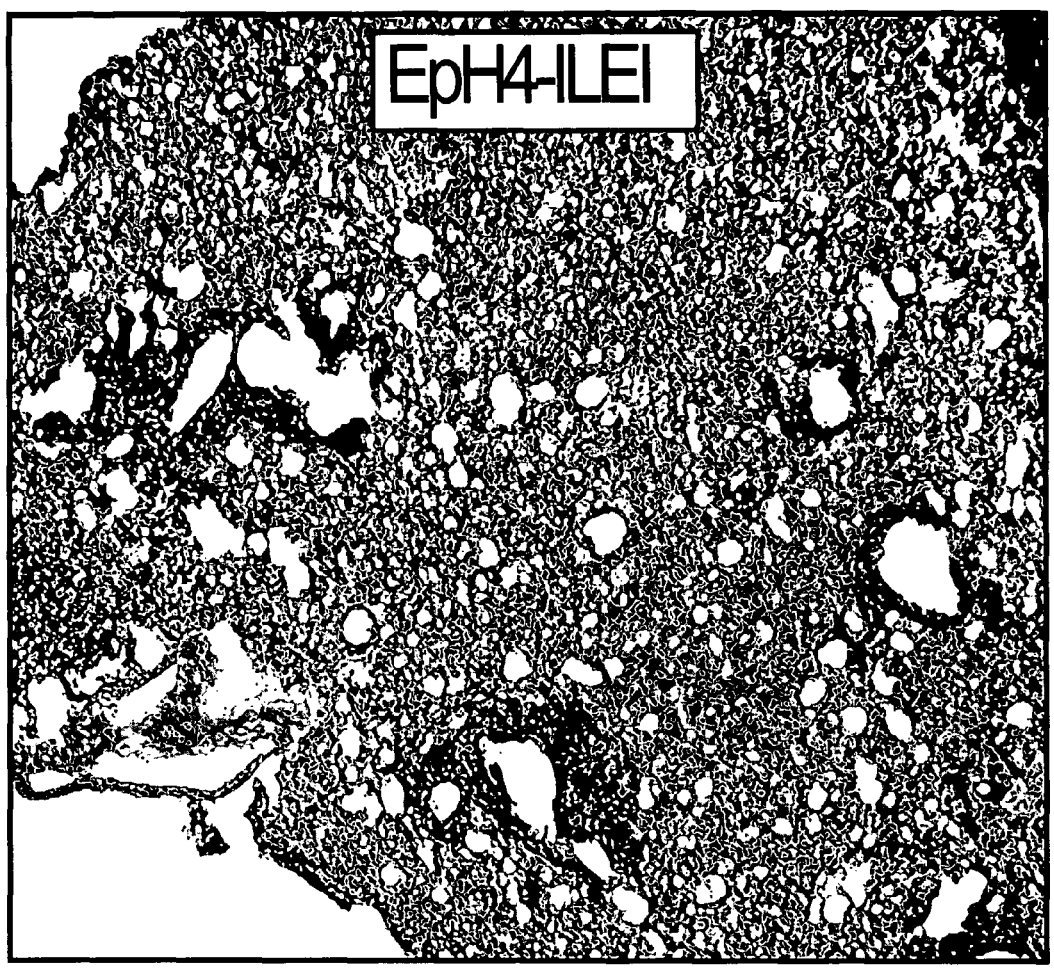
Figure 6E:
Figure 6F:
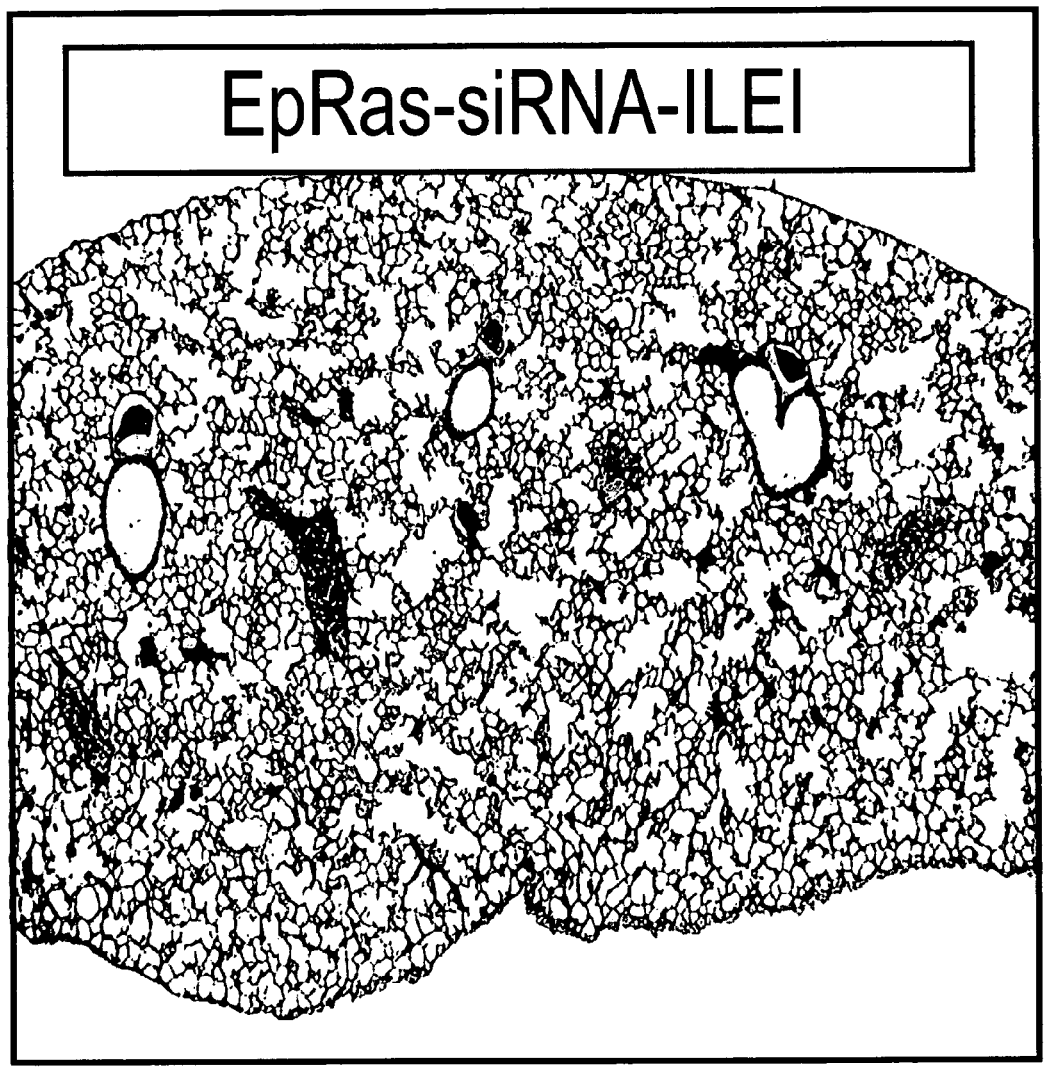

As some of the feature of metastatic cells are linked to the mesenchymal phenotype, the inventors investigated whether stable ILEI expression can promote metastasis. To address this question, apoptosis protected but not metastatic epithelial EpC40 cells and EpC40_ILEI cells were injected into the tail vein of nude mice and their capacity to metastasize to the lung was quantified. Consistent with the hypothesis, all 7 mice injected with EpC40_ILEI cells developed about 30 or more lung metastases (100% of animals). In contrast, one single metastasis was detected after injecting 8 mice with EpC40 cells expressing GFP in a retroviral expression construct (12.5% of animals) (FIG. 6a). Recultivated tumor cells were detected as GFP positive under a microscope. These results indicate that EpC40_ILEI cells must acquire the ability to survive in the blood circulation, evade and colonize distant organs, in contrast to their not metastatic EpC40 origins. FIG. 6 shows that ILEI induces metastasis formation, while knockdown of ILEI in metastatic tumor cells prevents metastasis. FIG. 6a: 50 000 cells of the cell types indicated were injected intravenously into nude mice and metastases evaluated after 2.5-12 weeks by counting metastases in serial lung sections. Average numbers of lung metastases per 10 tissue sections are shown. FIG. 6b: Almost complete suppression of metastases induced by EpRasXT cells by knockdown of ILEI after infection with ILEI-siRNA-expressing retroviruses. FIG. 6c: Injected EpRasXT-siRNA-ILEI cells seem to accumulate in blood vessels of the lung (arrows, red fluorescent protein-positive cells in multiple layers (left panel), compared to a normal lung blood vessel of control mice. FIG. 6d: Hematoxilin/Eosin (H&E) staining of lungs from mice injected with EpH4-ILEI cells show small-sized metastases around some blood vessels after 12 weeks. (e) Massive lung metastases caused by EpRas-XT induced after 2.5 weeks. No metastases are detectable in the lung 12 weeks after injection of EpH4 cells.

Example 10

ILEI Protein Knock Down Reduces Metastatic Capacity

Knock Down of the ILEI protein level in EpRas ex tumor cells (Western blot detection of ILEI is shown in FIG. 3c) significantly reduces the capacity to undergo EMT in collagen gel (FIG. 3d) and in vivo metastases after tail vein injection (FIG. 6a,b). Preliminary analysis of the lungs indicated that some of these cells accumulate in blood vessels but are unable to transmigrate the vessel wall or survive in the host tissue (FIG. 6c).

Example 11

Figure 9:
FIG. 9: Anti-ILEI antibody sera interferes with growth of EpRas organotypic structures
Figure 9:
Figure 9:
Figure 9:

Neutralizing Anti-ILEI Antibodies can Interfere with Tumor Cell Growth a) In a first experiment, methods for purification of antibody sera and cell treatment were used are described in (q). The obtained results indicate a reduced tumor cell growth on plastic plates when mesenchymal EpH4_ILEI cells are treated for 48 h with affinity purified anti peptide 2 (mouse sequence C-giktkspfeqhiknnketnkyeg) antibody sera. This effect was specific for mesenchymal cells and was not seen for epithelial EpH4 cells.

b) In a further experiment, EpRas cells were treated on plastic plates for four days with 5 ng/ml TGFβ to induce an invasive phenotype and seeded in collagen gel (2500 cells in 100 µL of 1.5% collagen matrix). A partial inhibition of the invasive phenotype and a decrease in the number of large sized collagen structures was observed when cells were treated for five days with the IgG fraction of ILEI immunized rabbit sera (total IgG concentration of 500 µg/ml). This effect was not seen with the same concentration of control IgG, raised from the sera of a non immunized rabbit For IgG isolation, sera was purified by Sepharose A, according to standard protocols. In FIG. 9, two pictures of collagen gel structures after treatment with anti ILEI IgG (left panels) and IgG control (right panels) are shown. Arrows on the left panels highlight the anti-ILEI effect detectable by smaller cell structures consisting of a low number of cells. These structures are mainly epithelial. The panels on the right represent structures of TGFβ-activated, invasive EpRas cells in collagen gel. This results indicates that functional blocking of ILEI by anti-ILEI antibodies can block aspects of cell invasion and inhibit the size growth of EpRas cell structures.

Example 12

ILEI is Expressed in Human Tumor Tissues

Figure 8:
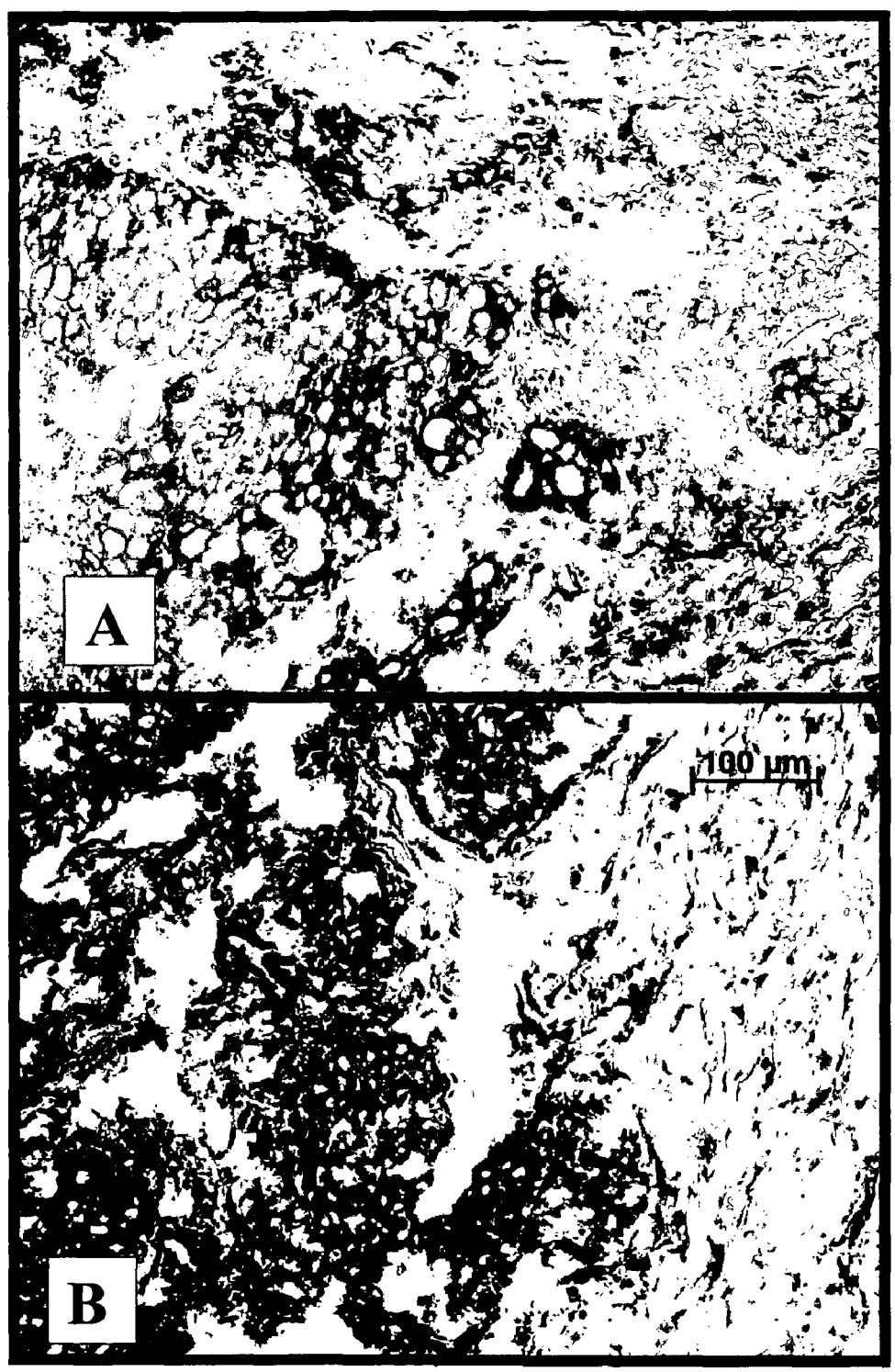
FIG. 8: Immunohistochemical detection of ILEI in human tumor specimens

To investigate the expression of ILEI in human tumor samples, immunohistochemistry in a panel of carcinomas of different origin was performed. As primary antibody for ILEI detection, an affinity purified rabbit polyclonal serum was used (see Example 11). This affinity purified antibody was shown to react with recombinant human ILEI (obtained by transient expression in Cos cells as described in Materials and Methods, j) in Western blot analysis. For immunohistochemistry, antibody concentrations between 1 µg/ml and 10 µg/ml were used. In all 28 tested specimens of invasive tumors (breast adenocarcinoma, colon adenocarcinoma, lung squamous cell carcinoma) expression of ILEI was detected. ILEI expression was observed in tumor cells and surrounding tumor stroma. These data demonstrate that ILEI is frequently expressed in human tumor tissues. FIG. 8 shows immunohistochemical detection of ILEI in human tumor specimens. An example of a lung squamous cell carcinoma (a) and a breast invasive ductal carcinoma (b) is shown. ILEI is predominantly expressed in tumor cells and, to a lower extent, also in tumor stroma.

Example 13

ILEI is Expressed in Single Cells in Smoked Rat Lungs

To investigate the effect of cigarette smoke on ILEI expression in rat lungs, male Sprague Dawley rats were used. For the following investigations, the smoke of 16 cigarettes "Rothändle" without filter were inhaled on 4 days and smoke of 8 cigarettes for one day per week by rats in a specifically designed cage.

Rats were treated with smoke for different time periods. Lungs from the following time points were investigated for ILEI expressing cells: 4 days (1 animal), 15 days (1 animal), 5 weeks (1 animal) 6 weeks (5 animals). The same number of control rats without smoke treatment was investigated. Sections of rat lungs for each timepoint and each animal were investigated for ILEI protein expression by immunhistochemistry as described above and compared to non-smoked rat lungs (day 4, 15 and week 5, 6).

Figure 10A:
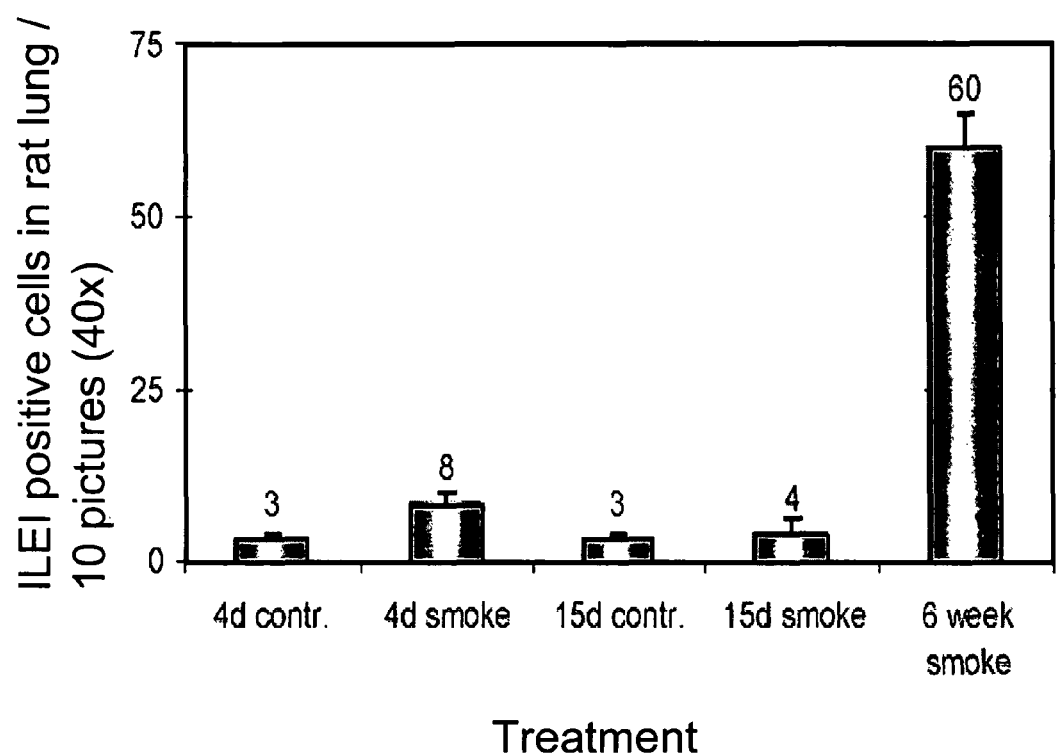
FIG. 10: Increase in the number of ILEI positive cells in smoked rat lungs
Figure 10B:

Initial analysis revealed an increase in the number of ILEI expressing cells after 5 and 6 weeks of smoking in 5 of 7 mice but not after shorter smoking times. The average number of ILEI positive cells of 10 pictures, obtained from one slide of non smoked rat lung for 4 and 15 days (=4 and 15 days contr.) and rat lungs after 4, 15 days and 6 weeks smoking are summarized in FIG. 10a. Two representative immunohistostainings of both, non smoked (upper panel) and 6 week smoked rat lungs are shown in FIG. 10b. ILEI positive cells are marked with an arrow in the lower panel.

Example 14

Generating ILEI Transgenic Mice for In Vivo Investigation of ILEI Function

A Cre-loxP based binary transgenic approach lacZ/chicken β-Actin promoter (Z/AP) as described by Ding et al., 2002, was employed to produce Z/AP-ILEI lines. Using this approach ILEI expression could be detected upon beta.geo cassette (lacZ/neomycin) excision.

LacZ expression is used for investigation of activity of the chicken B-Actin promoter prior to excision of the LacZ sequence which then leads to the expression of ILEI driven by the same promoter sequence.

For generation of the vector construct, the reading frame of ILEI cDNA (SEQ ID NO:3, starting with ATG) was amplified with additional XhoI and BglII restriction site overhangs by standard PCR technique. These sites were used to insert the ILEI coding sequence into the pCCALL vector, opened by XhoI/Bgl II (see U.S. Pat. No. 6,689,937).

This construct was inserted into a mouse germ line using standard techniques of oocyte microinjection, as described e.g. in U.S. Pat. No. 6,689,937.

If the expression of ILEI in the generated transgene mouse is low, either a complete genomic sequence injected as a YAC or chromosome fragment, a cDNA with either the natural promoter or a heterologous promoter, or a minigene containing all of the coding region and other elements found to be necessary for optimum expression are inserted stably into the mouse genome with the technique described above.

Analysis of the transgenic mice is done by standard histopathologic analysis (e.g. Hematoxilin/Eosin staining, immunohistostaining) of mouse embryos or organs or by cultivation of primary cells of different organs and analysis with standard assays (e.g. assays to investigate proliferation, transmigration, apoptosis, cell motility).

We claim:

1. An antibody or an antibody fragment which binds to a polypeptide which consists of the sequence set forth in SEQ ID NO: 10.

2. An antibody or an antibody fragment which binds to a polypeptide which consists of amino acids 189 to 211 of SEQ ID NO: 2 or SEQ ID NO: 4.

3. The antibody or the antibody fragment of claim 1, which is a polyclonal antibody.

4. The antibody of claim 1 or fragment thereof, which specifically binds to human ILEI (Interleukin-like EMT inducer).

5. The antibody or fragment thereof according to claim 1, which is a monoclonal antibody.

6. The antibody or fragment thereof of claim 5, which is a recombinant antibody.

7. The antibody or fragment thereof of claim 1, which is chimeric.

8. The antibody or fragment thereof of claim 1, which is humanized.

9. The antibody or fragment thereof according to claim 1, which is human.

10. The antibody fragment according to claim 1, which is a Fab fragment.

11. The antibody or fragment thereof of claim 1, which is conjugated to a therapeutic moiety or a radioactive metal ion.

12. A pharmaceutical composition comprising, as an active ingredient, an antibody or a fragment according to claim 1 and a pharmaceutically acceptable carrier.

13. The antibody or the antibody fragment of claim 2, which is a polyclonal antibody.

14. The antibody of claim 2 or fragment thereof, which specifically binds to human ILEI.

15. The antibody or fragment thereof according to claim 2, which is a monoclonal antibody.

16. The antibody or fragment thereof of claim 15, which is a recombinant antibody.

17. The antibody or fragment thereof of claim 2, which is chimeric.

18. The antibody or fragment thereof of claim 2, which is humanized.

19. The antibody or fragment thereof according to claim 2, which is human.

20. The antibody fragment according to claim 2, which is a Fab fragment.

21. The antibody or fragment thereof of claim 2, which is conjugated to a therapeutic moiety or a radioactive metal ion.

22. A pharmaceutical composition comprising, as an active ingredient, an antibody or a fragment according to claim 2 and a pharmaceutically acceptable carrier.

* * * * *